United States Patent
Poore et al.

(10) Patent No.: US 7,630,767 B1
(45) Date of Patent: Dec. 8, 2009

(54) SYSTEM AND METHOD FOR COMMUNICATING INFORMATION USING ENCODED PACING PULSES WITHIN AN IMPLANTABLE MEDICAL SYSTEM

(75) Inventors: John W. Poore, South Pasadena, CA (US); Gene A. Bornzin, Simi Valley, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 377 days.

(21) Appl. No.: 11/440,723

(22) Filed: May 24, 2006

Related U.S. Application Data

(63) Continuation-in-part of application No. 10/891,747, filed on Jul. 14, 2004, now abandoned.

(51) Int. Cl.
*A61N 1/372* (2006.01)
(52) U.S. Cl. .......................... 607/32; 607/60
(58) Field of Classification Search .............. 607/9, 607/14, 27, 60, 33
See application file for complete search history.

(56) References Cited

U.S. PATENT DOCUMENTS

| | | | | |
|---|---|---|---|---|
| 4,151,513 A | * | 4/1979 | Menken et al. | 340/870.24 |
| 4,256,115 A | * | 3/1981 | Bilitch | 607/9 |
| 4,407,289 A | * | 10/1983 | Nappholz et al. | 607/14 |
| 4,488,553 A | * | 12/1984 | Nappholz et al. | 607/14 |
| 4,488,554 A | * | 12/1984 | Nappholz et al. | 607/14 |
| 4,742,458 A | | 5/1988 | Nathans et al. | 364/417 |
| 4,886,064 A | | 12/1989 | Strandberg | 128/419 PG |
| 4,987,897 A | | 1/1991 | Funke | 128/419 PG |
| 4,989,602 A | | 2/1991 | Sholder et al. | |
| 5,243,977 A | | 9/1993 | Trabucco et al. | 607/10 |
| 5,280,792 A | | 1/1994 | Leong et al. | 128/702 |
| 5,782,885 A | | 7/1998 | Andersson | 607/17 |
| 5,797,399 A | | 8/1998 | Morris et al. | 128/705 |
| 5,814,089 A | | 9/1998 | Stokes et al. | 607/32 |
| 5,899,928 A | * | 5/1999 | Sholder et al. | 607/27 |
| 6,141,588 A | * | 10/2000 | Cox et al. | 607/9 |
| 6,144,879 A | | 11/2000 | Gray | 607/20 |
| 6,424,865 B1 | | 7/2002 | Ding | 607/9 |
| 6,512,952 B2 | | 1/2003 | Stahmann et al. | 607/9 |
| 6,553,261 B2 | * | 4/2003 | Thong | 607/27 |

(Continued)

OTHER PUBLICATIONS

NonFinal Office Action, mailed Oct. 2, 2006: U.S. Appl. No. 10/891,747.

(Continued)

*Primary Examiner*—Carl H Layno
*Assistant Examiner*—Luther G Behringer

(57) ABSTRACT

Techniques are provided for delivering cardiac pacing therapy to the heart of a patient using an epicardial left ventricular satellite pacing device in conjunction with primary pacemaker having at least a right ventricular pacing lead. In one embodiment described herein, right ventricular pulses generated by the primary pacemaker are detected by the satellite pacer and analyzed to determine the timing pattern employed by the primary pacemaker. The timing pattern is then used to specify the delivery times of epicardial left ventricular pulses so as to be synchronized with right ventricular pulses. In another embodiment described herein, the primary pacemaker modulates the right ventricular pulses to encode timing information, which is then detected and decoded by the satellite pacemaker. In this manner, biventricular pacing therapy, such as cardiac resynchronization therapy, may be conveniently delivered using a non-biventricular pacemaker in combination with an epicardial satellite pacer.

18 Claims, 14 Drawing Sheets

U.S. PATENT DOCUMENTS

| | | |
|---|---|---|
| 6,584,352 B2 | 6/2003 | Combs et al. |
| 6,628,988 B2 | 9/2003 | Kramer et al. ................. 607/9 |
| 6,643,546 B2 | 11/2003 | Mathis et al. .................. 607/9 |
| 6,694,188 B1 | 2/2004 | Kroll ........................... 607/14 |
| 6,704,602 B2 * | 3/2004 | Berg et al. .................... 607/60 |
| 6,885,889 B2 | 4/2005 | Chinchoy |
| 7,013,178 B2 * | 3/2006 | Reinke et al. ................ 607/60 |
| 7,425,210 B2 * | 9/2008 | Sweeney et al. ......... 604/891.1 |
| 2001/0041919 A1 | 11/2001 | Esler ........................... 607/27 |
| 2003/0100923 A1 | 5/2003 | Bjorling et al. ................ 607/9 |
| 2004/0172104 A1 | 9/2004 | Berg et al. |
| 2006/0136004 A1 * | 6/2006 | Cowan et al. ................. 607/33 |
| 2006/0241701 A1 * | 10/2006 | Markowitz et al. ............. 607/5 |

OTHER PUBLICATIONS

Final Office Action, mailed Dec. 26, 2007: U.S. Appl. No. 10/891,747.

Final Office Action, mailed Sep. 23, 2008: U.S. Appl. No. 10/891,747.

* cited by examiner

SYSTEM AND METHOD FOR COMMUNICATING INFORMATION USING ENCODED PACING PULSES WITHIN AN IMPLANTABLE MEDICAL SYSTEM

CROSS-REFERENCE TO RELATED APPLICATIONS

This application is a continuation-in-part (CIP) of U.S. patent application Ser. No. 10/891,747, filed Jul. 14, 2004, now abandoned, entitled "System and Method for Synchronizing Supplemental Pacing Pulses Generated by a Satellite Pacing Device with Primary Pulses Delivered by a Separate Pacing Device," which is incorporated by reference herein.

FIELD OF THE INVENTION

The invention generally relates to implantable cardiac stimulation systems, such as pacemakers or implantable cardioverter-defibrillators (ICDs), and in particular to systems employing both primary and satellite stimulation devices.

BACKGROUND OF THE INVENTION

Congestive heart failure (CHF) is a condition in which a weakened heart cannot pump enough blood to body organs. Heart failure may affect either the right side, left side, or both sides of the heart. As pumping action is reduced, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease. The weakened heart is also susceptible to potentially lethal ventricular tachyarrhythmias. One factor that contributes to heart failure is asynchronous activation of the ventricles wherein mechanical contraction is not properly coordinated thus compromising cardiac function.

One particularly promising technique for addressing heart failure is ventricular resynchronization therapy, which is a technique that seeks to normalize the asynchronous activation of the ventricles by delivering synchronized pacing stimulus to the ventricles using pacemakers or ICDs equipped with biventricular pacing capability. More specifically, the relative timing of pacing pulses delivered to the left and right ventricles is synchronized so as to help to improve overall cardiac function. This may have the additional beneficial effect of reducing the susceptibility to life-threatening tachyarrhythmias. Typically, an interventricular delay value is adjusted by a physician to "resynchronize" the ventricles and improve cardiac function for the patient. The interventricular delay specifies the time delay between delivery of a right ventricular (RV) pacing pulse and a left ventricular (LV) pacing pulse. The RV-LV interventricular delay may be positive, i.e. the RV pulse is delivered before the LV pulse or may be negative, i.e., the LV pulse is delivered before the RV pulse. Ventricular resynchronization therapy is one form of cardiac resynchronization therapy (CRT). Ventricular resynchronization therapy, CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing."

Unfortunately, when fitting a patient with an implantable biventricular pacing device, it can be difficult to pass a left-side lead into the coronary sinus vein, or the smaller final destination veins, or to keep it in stable position. Accordingly, there is a need for alternative techniques of applying electrical stimulus to the left ventricle, particularly for use in delivering CRT but also for use in delivering other forms of biventricular pacing therapy as well. U.S. patent application Ser. No. 10/408,198 to Kroll, entitled "Implantable Cardiac System with Master Pacing Unit and Slave Pacing Unit," filed Apr. 3, 2003, is directed to solving these and other problems. This patent application is incorporated by reference herein. In the system described by Kroll, a satellite or "slave" pacing device is mounted epicardially on the left ventricle for use in conjunction with a primary or "master" pacing device having a RV pacing lead. The primary pacing device delivers all RV pacing pulses, whereas the epicardial satellite pacing device delivers all LV pacing pulses. In this manner, a lead need not be implanted within the left ventricle, thus simplifying implantation and reducing any risks associated with LV lead placement.

In one specific example described by Kroll, the satellite pacing device detects RV pacing pulses delivered by the primary device, then delivers LV pacing pulses following a predetermined time delay. Using this system, CRT therapy may be delivered so long as the RV-LV interventricular delay is positive, i.e. so long as the right ventricle is to be paced prior to the left ventricle. In order to allow the left ventricle to be paced before the right ventricle, the patent application of Kroll sets forth an alternative implementation wherein the primary pacing device transmits control signals directly to the satellite pacing device for controlling the satellite device to deliver a LV pacing pulse prior to each RV pulse delivered by the primary pacing device. In other words, once the primary device has determined when it will deliver the next RV pacing pulse, it sends a control signal to the satellite device controlling that device to deliver an LV pacing pulse at a point in time shortly prior to the upcoming RV pacing pulse. In one of the specific examples described therein, the control signals are transmitted via wireless telemetry.

Although the systems and techniques described by Kroll represent a significant improvement over predecessor systems, there is room for further improvement. In particular, it would be desirable to provide a primary/satellite pacing system that does not require control signals to be transmitted via telemetry from the primary device to the secondary device to allow LV pulses to be delivered prior to RV pulses. To provide for transmission of control signals, the primary device and the secondary device must be equipped with suitable signal transmission/reception telemetry components. This increases the cost, size, weight and complexity of both of the devices and causes a greater drain on their power supplies. Also, when implemented using wireless telemetry, wireless signals generated by external devices can potentially interfere with signals transmitted from the primary device to the satellite device, possibly resulting in a failure of the satellite device to properly deliver needed LV pacing signals. In addition, the wireless signals of the implanted system can potentially interfere with the operation of external devices.

Moreover, many patients who might benefit from CRT already have RV pacing devices implanted therein. It would be desirable to instead provide a "stand-alone" satellite pacing device that could simply be used in combination with the existing device, so as to eliminate the need to remove the existing device and replace it with one specifically equipped with the capability for transmitting the aforementioned control signals to the satellite pacing device. A significant problem however is that, as already noted, it is often necessary for LV pacing pulses to be delivered prior to RV pacing pulses. Without the capability of the primary device to communicate the aforementioned control signals to the satellite device, it does not appear that the satellite device would be capable of operating in situations wherein LV pacing pulses need to be delivered prior to RV pacing pulses.

The above-referenced parent patent application to Poore et al. described an invention that solved these problems. Briefly, techniques set forth in Poore et al. provide for delivering cardiac pacing therapy to the heart of a patient using an epicardial left ventricular satellite pacing device in conjunction with an otherwise conventional pacemaker having a right ventricular pacing lead. Right ventricular pulses generated by the pacemaker are detected by the satellite pacer and analyzed to determine the timing pattern employed by the pacemaker. Then the timing pattern is used to specify the delivery times of epicardial left ventricular pulses so as to be synchronized with right ventricular pulses.

By first determining the timing pattern of the primary pulses, supplemental pulses may thereby be delivered in synchronization with expected upcoming primary pacing pulses. Synchronization may be subject to a predetermined time delay, which may set, for example, to specify that the supplemental pulses are to be delivered shortly prior to corresponding primary pulses. In this manner, synchronization is achieved between supplemental pacing pulses and primary pacing pulses while incorporating a "negative" primary-to-supplemental time delay, but without requiring transmission of control signals directly from the primary pacing device to the satellite device. Alternatively, as needed, the delay may be set to specify that the supplemental pulses are to be delivered shortly after corresponding primary pulses, or simultaneous therewith. In any case, by having the satellite pacer decode the timing pattern of the primary pacer, biventricular pacing therapy may be conveniently delivered using an otherwise conventional non-biventricular pacemaker in combination with the improved epicardial satellite pacer.

Although the techniques of the parent application are effective, additional or alternative techniques for solving the problems described above would also be desirable. In particular, it would be desirable to provide an alternative technique that permits the primary pacer to communicate primary pulse timing information to the satellite pacer (1) without requiring that the satellite pacer to decode the timing pattern of a sequence of primary pacing pulses and also (2) without requiring the primary pacer to transmit control signals via wireless telemetry to the satellite pacer. It is to this end that the present invention is primarily directed.

SUMMARY

Techniques are described herein for communicating information between first and second implantable medical devices within a patient, such as between a primary pacer and a satellite pacer. In method embodiment, a therapeutic electrical stimulation pulse is generated using the first device, with the stimulation pulse encoded with information to be communicated to the second device. The encoded therapeutic stimulation pulse is then delivered by the first device to patient tissue. The therapeutic stimulation pulse is detected within tissues of the patient using the second device, which decodes the detected pulse to extract the encoded information. By encoding information with the therapeutic stimulation pulse itself, information is thereby conveniently communicated from the first device to the second device without the need for wireless telemetry.

In an example wherein the first device is a primary cardiac pacer and the second device is a secondary or satellite cardiac pacer, the primary cardiac pacer delivers an encoded cardiac pacing pulse to cardiac tissue with a pulse magnitude sufficient to depolarize a portion of cardiac tissue. The satellite pacer detects a far-field version of the encoded cardiac pacing pulse and decodes the pulse to extract the information encoded therein. For example, the primary pacer may be a non-biventricular pacer equipped to deliver RV pacing pulses via endocardial electrodes implanted within the RV; whereas the satellite pacer may be an epicardial LV satellite pacer equipped to deliver synchronized pacing pulses to the LV for the purposes of achieving biventricular pacing.

In one particular example, the RV pacing pulses generated by the primary pacer are encoded with information representative of a timing pattern of upcoming RV pulses. The satellite pacer then determines the timing pattern for delivery of LV pulses so as to synchronize the LV pulses with the RV pulses in accordance with CRT techniques. The timing pattern of the RV pulses may specify, for example, the intervals between successive RV pacing pulses, i.e. the RV pacing rate. The timing pattern for the LV pulses may specify, for example, an interventricular RV-LV delay value. The interventricular delay may be set—based on the needs of a particular patient—to positive values, negative values, or to zero. In another example, the RV pacing pulses generated by the primary pacemaker are additionally encoded with control information for controlling the satellite pacer, such instructions as indicating whether LV pacing should be activated or deactivated.

Preferably, the RV pulses are encoded with information by modulating the shape of the RV pulse. For example, the pulse may be modulated to include a sequence of individual pulse portions collectively configured to digitally encode the information. Typically, the individual pulse portions have durations in the range of 15-30 microseconds ($\mu$s), whereas the total pulse has a duration in the range of 0.2-2.0 milliseconds (ms). In one specific example, the individual pulse portions are of equal duration but the relative spacing between the pulse portions is modulated to digitally encode the information. In another specific example, the relative spacing is uniform but the relative width of the individual pulse portions is modulated to digitally encode the information. Other encoding techniques, however, can be employed as well that do not necessarily require modulating the shape of the pulse.

BRIEF DESCRIPTION OF THE DRAWINGS

The above and further features, advantages and benefits will be apparent upon consideration of the descriptions below taken in conjunction with the accompanying drawings, in which.

DETAILED DESCRIPTION OF THE PREFERRED EMBODIMENTS

Figure 1:
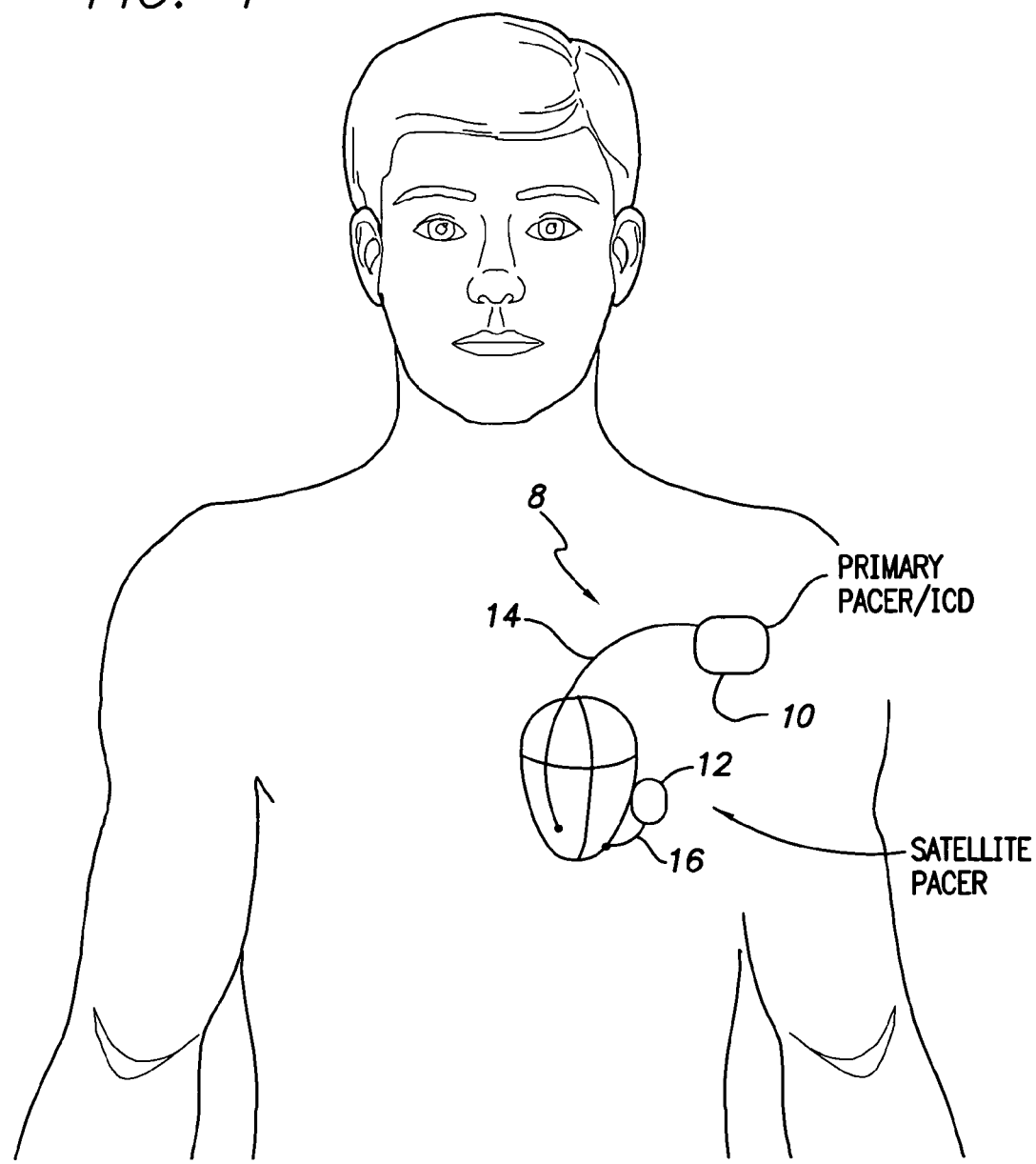
FIG. 1 illustrates pertinent components of an implantable cardiac stimulation system having a primary pacing device and a separate supplemental pacing device.

The following description includes the best mode presently contemplated for practicing the invention. The description is not to be taken in a limiting sense but is made merely to describe general principles of the invention. The scope of the invention should be ascertained with reference to the issued claims. In the description that follows, like reference numerals or reference designators will be used to refer to like parts or elements throughout. FIGS. 1-9 are generally directed to techniques for allowing a satellite pacer to automatically determine the timing pattern of primary pacing pulses based on a sequence of such pulses. FIGS. 10-16 are generally directed to techniques for allowing a primary pacer to communicate timing and other information to a satellite pacer via modulated pacing pulses.

Overview of Primary/Satellite Pacing System

Figure 7:
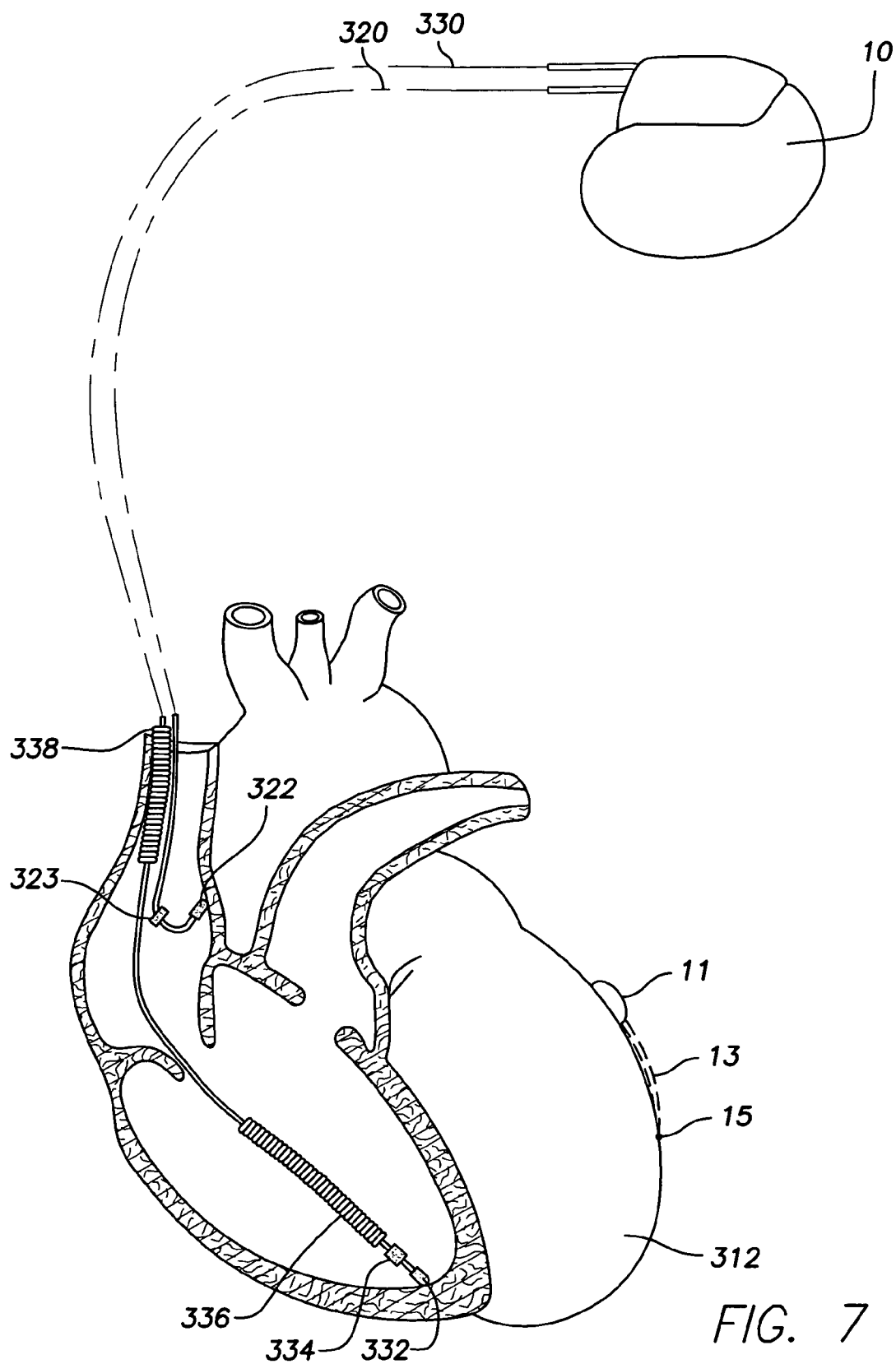
FIG. 7 is a simplified, partly cutaway view illustrating of an exemplary implementation of the implantable cardiac stimulation system of FIG. 1 employing a primary pacing device with leads implanted into the heart of a patient for delivering stimulation therapy to the right atria and right ventricle and a separate satellite pacing device with a lead mounted epicardially on the left ventricle for delivering stimulation therapy to the left ventricle.

FIG. 1 illustrates an implantable cardiac stimulation system 8 having a primary pacing device 10 and a "stand-alone" epicardial satellite pacing device 12, collectively capable of delivering CRT or other cardiac stimulation therapies to the heart of a patient. Primary pacing device 10 is a pacer/ICD or other cardiac stimulation device that incorporates internal components (shown in FIG. 8) for controlling delivery of therapy at least to the right ventricle of the heart. To this end, pacer/ICD 10 detects signals from cardiac pacing leads—one of which (an RV pacing lead 14)—is shown in FIG. 1. A complete set of exemplary pacing leads is illustrated in FIG. 7. In response to the detected signals, the pacer/ICD delivers cardiac pacing therapy via the RV lead. Pacing pulses delivered by the primary pacer/ICD are referred to herein as primary pacing pulses. Satellite Pacer 12 includes at least one epicardial lead 16 for sensing far-field electrical signals in the heart and for delivering LV pacing signals, which are referred to herein as supplemental pacing signals. Note that the FIG. 1 is merely a stylized representation of the implanted system. The sizes, shapes and implantation locations of the various components are merely exemplary.

As will be explained below in connection with FIGS. 2-9, the satellite pacer may be equipped to monitor far-field electrical signals detected using the epicardial electrode to detect a series of primary pacing pulses generated by the primary pacer/ICD. The satellite pacer then examines the relative timing of the primary pacing pulses to determine the timing pattern of the primary pacing pulses to allow synchronization of supplemental pacing pulses to upcoming primary pacing pulses. As will be explained below in connection with FIGS. 10-16, the satellite pacer may alternatively (or additionally) be equipped to decode information encoded within primary pacing pulses that is representative of the timing pattern of the primary pacing pulses to likewise allow synchronization of supplemental pacing pulses to upcoming primary pacing pulses.

In either case, by properly synchronizing the supplemental pulses delivered epicardially to the left ventricle with the primary pulses delivered internally to the right ventricle, the satellite pacer is thereby capable of enhancing the functionality of the implanted system to provide biventricular pacing therapy such as CRT. Advantageously, the satellite pacer is capable of synchronizing the supplemental pacing pulses with the primary pacing pulses without requiring any information to be transmitted directly from the primary pacer/ICD to the satellite pacer via wireless telemetry.

Hence, in some implementations described herein (FIGS. 2-9), the satellite pacer is a true stand-alone device, which can be used with otherwise conventional non-biventricular pacer/ICDs to enhance their functionality. This allows, for example, the satellite pacer to be implanted within a patient already having a non-biventricular pacing device implanted therein, without requiring the original device to be removed and replaced with a new device specifically equipped to operate in conjunction with the satellite pacer. In addition, the satellite device is advantageously implanted within patients having biventricular pacing devices employing LV leads that have failed. As such, the addition of the epicardial satellite device allows a resumption of biventricular pacing, without requiring the original LV lead to be removed from the left ventricle and replaced with a new LV lead, which is a potentially risky procedure.

In other implementations described herein (FIGS. 10-16), the satellite pacer is used in conjunction with a non-biventricular pacer/ICD that is modified to encode timing information with its pacing pulses. This allows the satellite pacer to quickly determine the timing pattern being used by the primary pacer so as to more quickly respond to any changes in the timing pattern, without the need for any conventional wireless telemetry. As will be appreciated, pulse encoding allows a wide variety of other information and/or commands to be communicated from the primary pacer to the satellite pacer, again without the need for conventional wireless telemetry.

Although FIG. 1 illustrates a satellite pacer mounted to the epicardium of the left ventricle, principles of the invention may be exploited in connection with satellite devices mounted to other chambers of the heart as well, as well as to other implantable devices not necessarily provided for pacing the heart.

Primary Pulse Sequence Analysis Techniques

Figure 2:
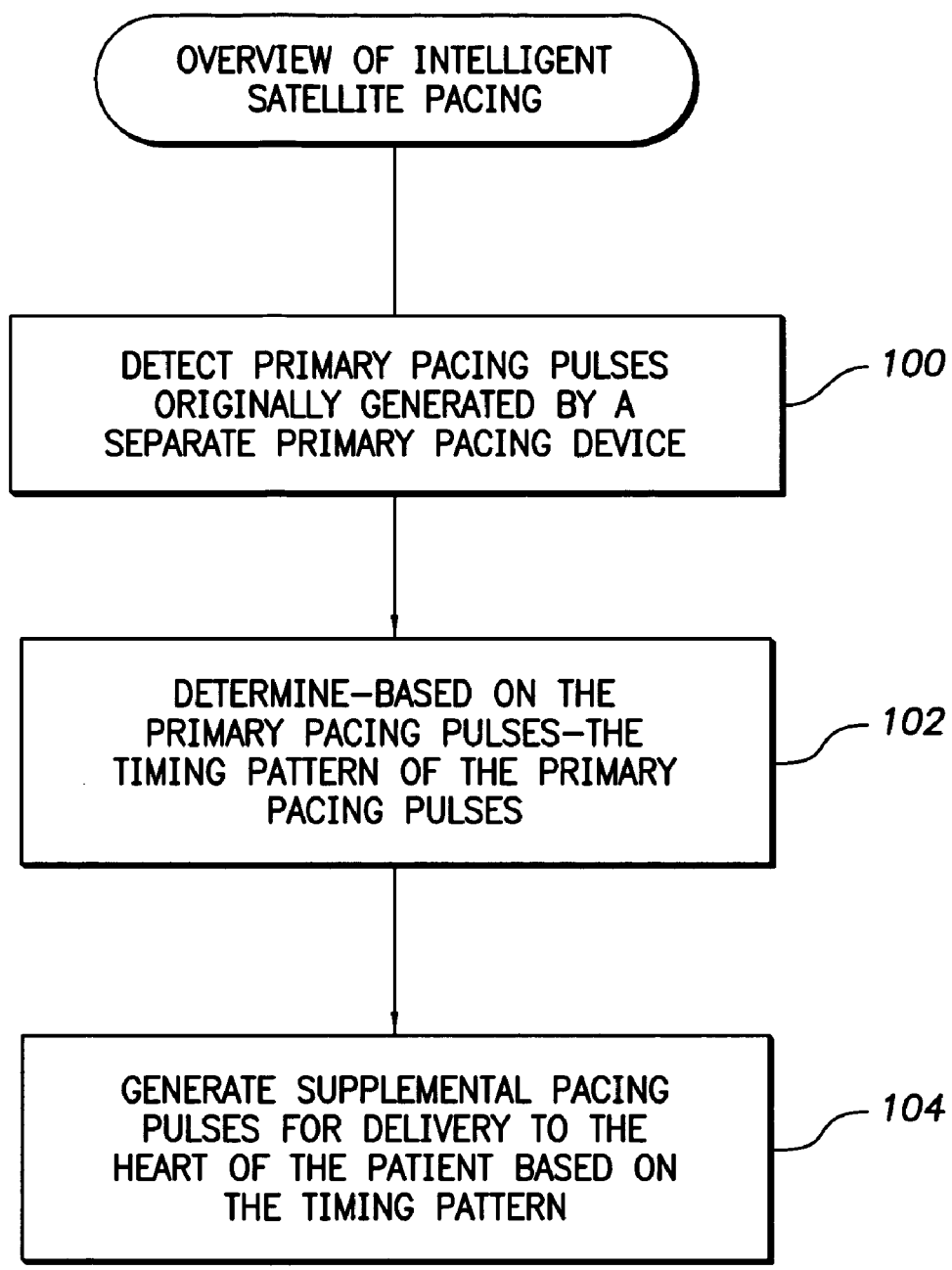
FIG. 2 is a flow diagram providing an overview of a first exemplary technique for delivering pacing therapy using the system of FIG. 1, wherein the supplemental pacing device intelligently synchronizes supplemental pacing pulses to primary pacing pulses generated by the primary pacing device by analyzing a series of primary pulses to determine a timing pattern.

Referring now to FIGS. 2-9, techniques for allowing a satellite pacer to determine timing sequences of primary pacing pulses will now be described. FIG. 2 provides an overview of the technique. Initially, at step 100, the satellite pacer detects primary pacing pulses originally generated by the primary pacer/ICD. Then, at step 102, the satellite pacer determines—based on the primary pacing pulses—the timing pattern of the primary pacing pulses. By synchronization, it is meant that the supplemental pulses are delivered at a specified time a relative to the primary pulses, which may be either before, during, or after corresponding primary pacing pulses. Next, at step 104, the satellite pacer generates supplemental pacing pulses for delivery to the heart of the patient based upon the timing determined at step 102. In this manner, the timing of the supplemental pulses is determined based on detected primary pulses without requiring any timing information to be transmitted directly from the primary pacer/ICD to the satellite pacer.

Figure 3:
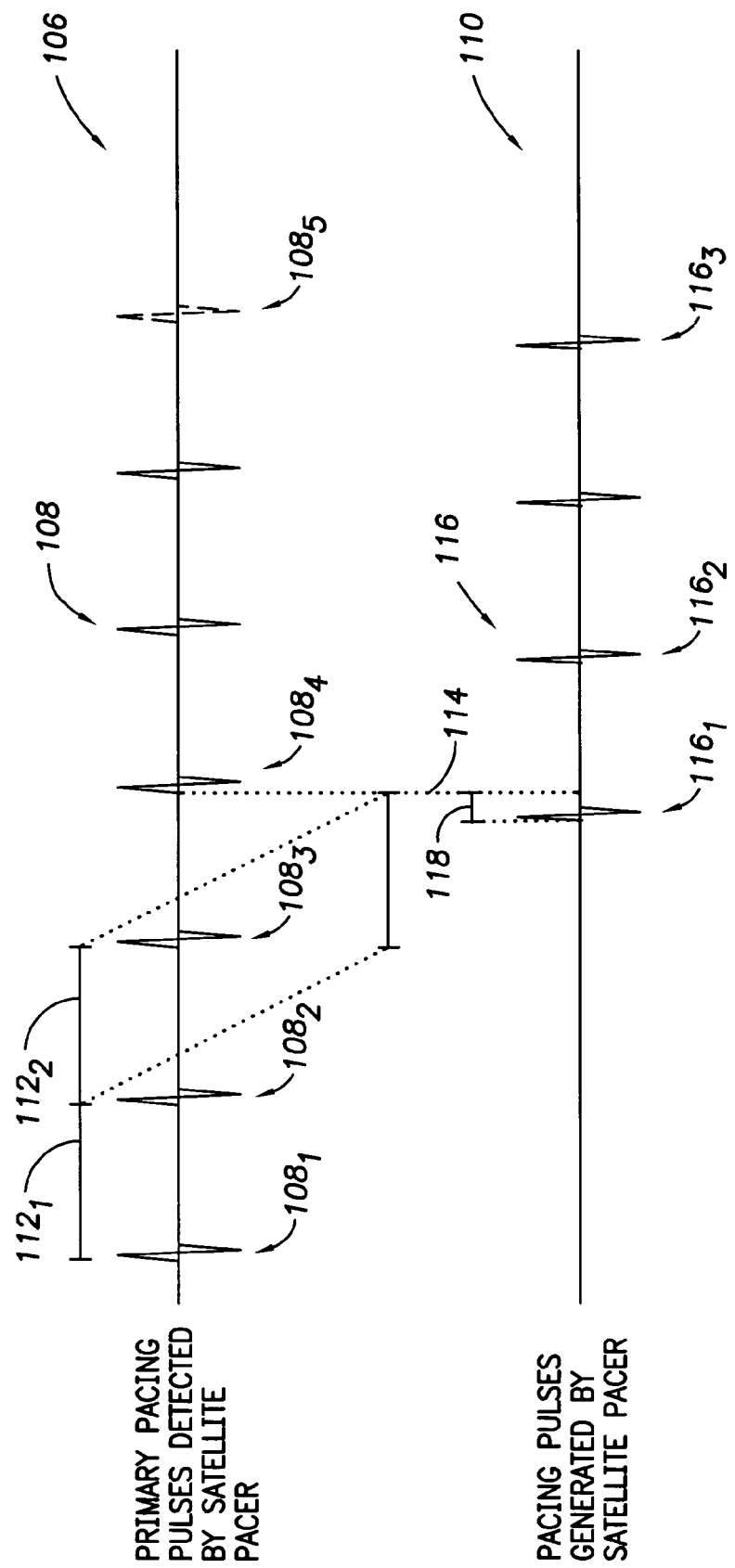
FIG. 3 is a stylized diagram of exemplary pacing pulses delivered by the primary and satellite devices of FIG. 1.

The technique is illustrated in FIG. 3. A first timing diagram 106 illustrates exemplary primary pacing pulses (e.g. RV pacing pulses) detected by the satellite pacer via its epicardial lead. The pacing pulses are generally denoted by reference numeral 108, with indices attached to identify particular pacing pulses. A second timing diagram 110 illustrates supplemental pacing pulses generated by the satellite pacer (e.g. LV epicardial pacing pulses). In the example of FIG. 3, the satellite pacer examines the timing of the first three primary pacing pulses $108_1$, $108_2$ and $108_3$ and calculates the time delays therebetween. The time delay between the first two pulses is identified by interval $112_1$. The time interval between the second two pulses is identified by interval $112_2$. In this particular example, the two intervals are identical indicating that the primary pacer is probably delivering primary pacing pulses at a constant rate. Accordingly, the satellite pacer then calculates the time at which the next primary pulse $108_4$ is expected to be delivered. This time is identified by dotted line 114. Based on this expected time, the satellite pacer determines the appropriate time for delivering a first supplemental pulse $116_1$. In this example, a negative RV-LV interventricular delay value is employed, represented by interval 118. In other words, the supplemental pulse is to be delivered shortly prior to the next expected primary pulse. The interventricular time delay is programmed into the supplemental pacer with the value set, based on the needs of the particular patient, to improve cardiac function.

After the supplemental pulse is delivered, the satellite pacer verifies that the next primary pulse ($108_4$) was delivered at the expected time. If so, another supplemental pulse $116_2$ is delivered with the same relative timing. So long as primary pulses continue to be detected at the expected times, the satellite pacer continues to generate and deliver additional supplemental pulses, each one synchronized with a corresponding primary pulse, but delivered shortly prior thereto. In other examples, based on the needs of the patient, a positive RV-LV interventricular delay may instead be used or no interventricular delay may be used. If positive, then the satellite pacer delivers the supplemental pulses shortly following the next expected primary pulses. If the interventricular delay set to zero, then the supplemental pulses are generated substantially simultaneous with the corresponding expected primary pulses.

If, any point, additional primary pulses cease to be detected, i.e. the primary pacer/ICD stops delivering RV pacing pulses, the satellite pacer likewise stops delivering supplemental pacing pulses to the left ventricle. This is also shown in FIG. 3. A primary pulse $108_5$, shown in phantom lines, is expected to be delivered, but is not detected. Since a negative interventricular delay is employed, an extra supplemental pacing pulse $116_3$ is delivered before the satellite pacer can detect that the expected primary pulse did not occur. If a positive interventricular delay is instead employed, the satellite pacer typically has sufficient time to detect the lack of the expected primary pulse and suspend delivery of additional supplemental pacing pulses. Thus, at most, one extra supplemental pulse is generated that is not synchronized with a corresponding primary pulse. If the rate of the primary pacing pulses changes, the satellite pacer detects that the primary pulse was not delivered at the expected time, then suspends delivery of additional pacing pulses until it can determine the new rate based upon a series of primary pulses detected at that rate. Thereafter, the satellite pacer resumes delivery of supplemental pulses, again synchronized with the primary pulses, but now at the new rate.

With primary pacing pulses delivered at a constant rate, the satellite pacer need only examine two primary pulses to determine the primary pulse rate. However, three pulses are preferred so as to allow confirmation that the rate appears constant. So long as each inter-pulse interval remains the same, the satellite pacer presumes that the primary pacing rate is constant. Alternatively, primary pacing pulses may be delivered in accordance with more complicated pacing patterns, such as overdrive pacing patters or patterns designed to enhance R-R variability. If so, the satellite pacer will typically require a larger number of primary pulses before it can decode or "decipher" the pattern of the primary pulses so that it can then reliably predict timing of upcoming primary pulses and synchronize the supplemental pulses. This will be described in greater detail below.

Thus, FIGS. 2-3 provide an overview of the pattern recognition-based intelligent satellite pacing techniques of the invention. With reference to the following figures, specific examples for use in performing CRT will now be described. The timing diagrams of FIG. 3 are merely stylized representations and should not be construed as representing actual clinically detected signals. The horizontal (time) axis and the vertical (magnitude) axis are both in arbitrary units.

Figure 4:
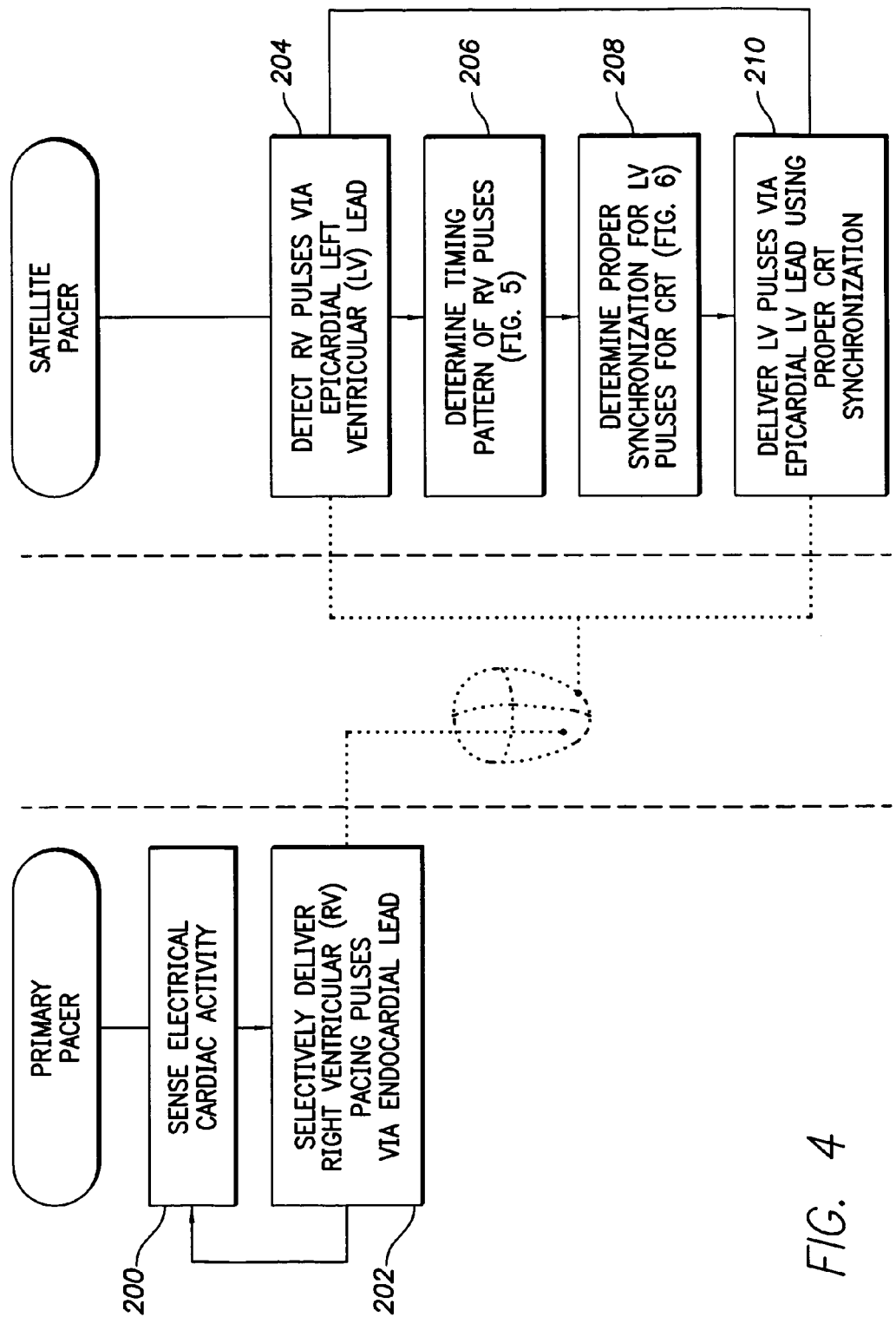
FIG. 4 is a flow diagram providing an exemplary technique for delivering synchronized pacing for providing CRT using the system of FIG. 1.

FIG. 4 provides an overview of steps performed by both the primary pacer and the satellite pacer for an implementation directed primarily to delivering CRT. Steps performed by the primary pacer are shown on the left. Steps performed by the satellite pacer are shown on the right. In addition, a stylized representation of a heart is provided within the figure. At step 200, the primary pacer senses electrical cardiac activity using its RV lead then, at step 202, selectively delivers RV pacing pulses via the RV lead. Meanwhile, at step 204, the satellite pacer detects of the RV pulses via its epicardial LV lead and, at step 206, determines the timing pattern of the RV pulses. Exemplary techniques based on pattern recognition are summarized to below with reference to FIG. 5. Next, at step 208, the satellite pacer determines the proper synchronization for LV pulses for delivery epicardially to the left ventricle in accordance with CRT techniques. An exemplary technique for determining synchronization is described below with reference to FIG. 6. Then, at step 210, the satellite pacer delivers LV pacing pulses via the epicardial LV lead using proper CRT synchronization so as to improve the cardiac function of the patient.

As shown in FIG. 4, the steps performed by the primary pacer and the steps performed by the satellite pacer are repeated, each in its own loop. While steps 200 and 202 are repeated, the primary pacer selectively activates and deactivates RV pacing while selectively adjusting the RV pacing rate to, for example, respond to various arrhythmias, to deliver overdrive pacing therapy, and the like. Meanwhile, the satellite pacer detects and responds to changes in RV pacing to automatically adjust the timing of its LV pacing pulses to remain substantially in synch with any RV pulses being delivered. As already noted, if RV pacing is suspended, the satellite pacer likewise suspends delivery of the LV pulses. LV pulses are not again delivered until the primary pacer reactivates RV pacing and the satellite pacer has a chance to process enough new RV pulses time intervals to be able to ascertain the timing pattern of the new RV pulses so that it may then deliver supplemental pacing pulses in synchronization therewith.

Figure 5:
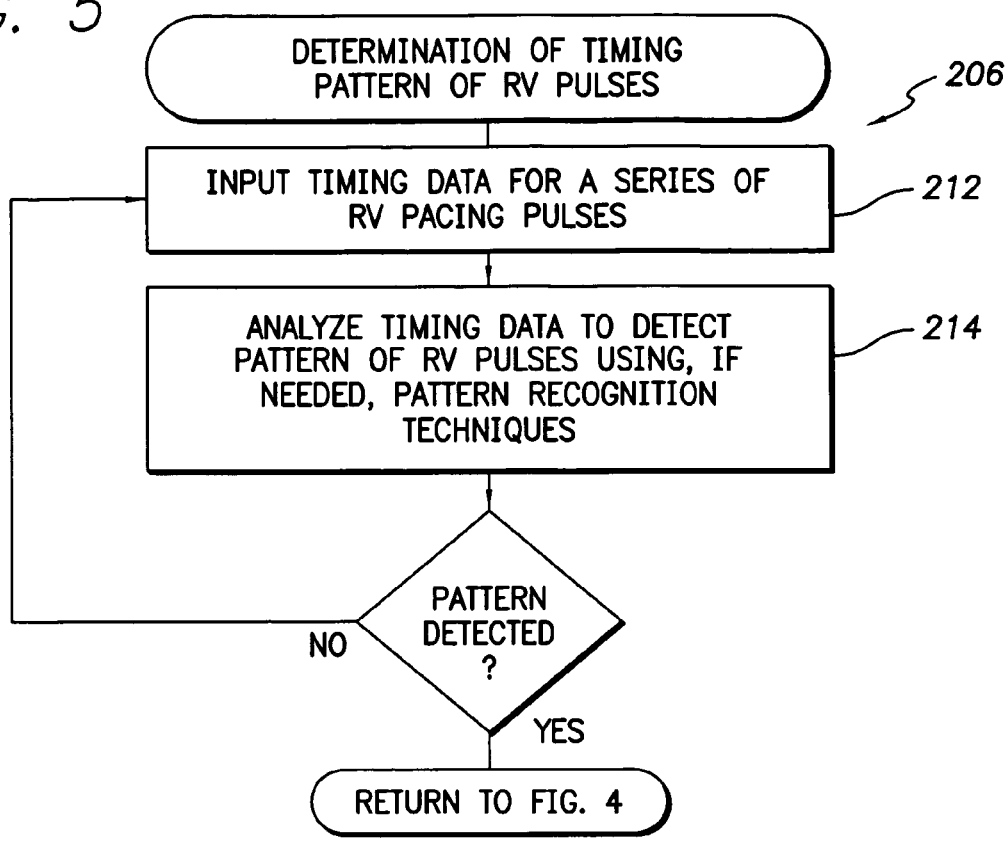
FIG. 5 is a flow diagram providing an exemplary technique for determining the timing sequence of primary pulses for use with the technique of FIG. 4.

Turning now to FIG. 5, exemplary techniques for determining the timing pattern or sequence of RV pulses (or other primary pulses) will be discussed. Initially, at step 212, a synchronization controller of the satellite pacer inputs timing data for a series of RV pacing pulses (detected at step 204) then, at step 214, the synchronization controller analyzes the timing data to detect the pattern of primary pulses. Assuming the pattern has been detected, processing then returns to step 208 of FIG. 4. Otherwise, the synchronization controller continues to input additional timing data corresponding to additional primary pulses in an effort to decode or decipher the timing sequence of the primary pulses.

The timing data input at step 212 preferably includes the individual times of individual RV pulses. Based on the times, the synchronization controller determines the duration of inter-pulse intervals. In an exemplary embodiment, assuming the intervals remain constant over at least three RV pulses, a constant RV rate is presumed so that LV pacing can commence. Timing data for new RV pulses is input and analyzed to verify the RV rate is indeed constant. If the inter-pulse intervals are not constant, the synchronization controller then seeks to determine whether the RV rate is being adjusted by the primary pacer using a linear rate increase or decrease by, for example, determining if the duration of the inter-pulse intervals are increasing or decreasing linearly from one RV pulse to the next. In the exemplary embodiment, assuming the rate of change in the duration of the intervals remains constant over at least four RV pulses, a constant RV rate of change is presumed. Again, timing data for new RV pulses is input and analyzed to verify the RV rate of change is indeed constant.

Linear RV rate changes may occur, for example, if the primary pacer is performing ventricular overdrive pacing. With DVO, a ventricular overdrive rate is maintained constant for some period of time, then is gradually reduced until some number of intrinsic "breakthrough" ventricular beats are detected, at which point the overdrive rate is bumped up to a higher rate. By tracking linear rate decreases, the synchronization controller is thereby able to track the overdrive rate and deliver LV pulses in synchronization therewith, at least until the overdrive rate is bumped up, at which point the synchronization controller briefly suspends LV pacing until it can determine the new overdrive rate. Similarly, the synchronization controller is able to track other linear rate changes.

If the RV rate is not found to be constant (or not changing linearly), the synchronization controller inputs still more timing data in an effort to determine the timing pattern used by the primary device. Otherwise conventional pattern recognition techniques or pattern matching techniques may be employed to analyze the data to identify pacing patterns therein. Pattern recognition techniques, pattern matching techniques, and related techniques are described in the following patents and patent applications: U.S. Pat. No. 4,742,458 Nathans et al. entitled "Method and Apparatus for Performing Pattern Recognition Analysis"; U.S. Pat. No. 5,280,792 to Leong et al., entitled "Method and System for Automatically Classifying Intracardiac Electrograms"; U.S. Pat. No. 5,782,885 to Andersson, entitled "Rate Responsive Heart Stimulation Device Using Neural Network and IEGM Classifier"; U.S. Pat. No. 5,797,399 to Morris et al., entitled "Method and Apparatus for Identifying and Correctly Responding To Abnormal Heart Activity"; U.S. Patent Application 2003/0100923 A1 of Bjorling et al., entitled "Method and Circuit for Detecting Cardiac Rhythm Abnormalities by Analyzing Time Differences Between Unipolar Signals from a Lead with a Multi-Electrode Tip"; U.S. Patent Application 2001/0041919 A1 to Esler, entitled "Cardiac Rhythm Management System with Prevention of Double Counting of Events."

With pattern recognition techniques, almost any timing pattern employed by the primary pacer/ICD can eventually be decoded by the satellite pacer based. In circumstances where the primary pacer/ICD delivers primary pulses in accordance with a relatively complicated pattern, perhaps to achieve some minimum degree of R-R variability, then a fairly large number of primary pulses may need to be analyzed for the satellite pacer determines the timing pattern. Once the timing pattern has been decoded, however, LV pulses can be delivered in synchronization therewith indefinitely (so long as the primarily device continues to employs the same timing pattern.)

In some cases, the pacer/ICD may be configured to adjust the timing of RV pacing pulses so to achieve a random or pseudo-random degree variability, in which case the satellite pacer will not be able to determine an exact timing pattern. See, for example, U.S. Pat. No. 6,694,188, Kroll, entitled "Dynamic Control of Overdrive Pacing Based on Degree of Randomness within Heart Rate." If so, then supplemental pacing pulses are not generated until a non-random timing pattern is again detected. Alternatively, the physician, while programming the operation of the satellite pacer, simply reprograms the primary pacer to deactivate any random or pseudo-random pacing techniques. Preferably, anytime the satellite pacer is unable to decode the pacing pattern of the primary pacing pulses, the satellite pacer records appropriate diagnostic information for subsequent review by the physician who can then, if warranted, reprogram the primary pacer (assuming it can be reprogrammed) to employ a pacing pattern that will permit the satellite pacer to decode the pattern. Once the timing pattern has been determined, processing returns to FIG. 4.

Figure 6:
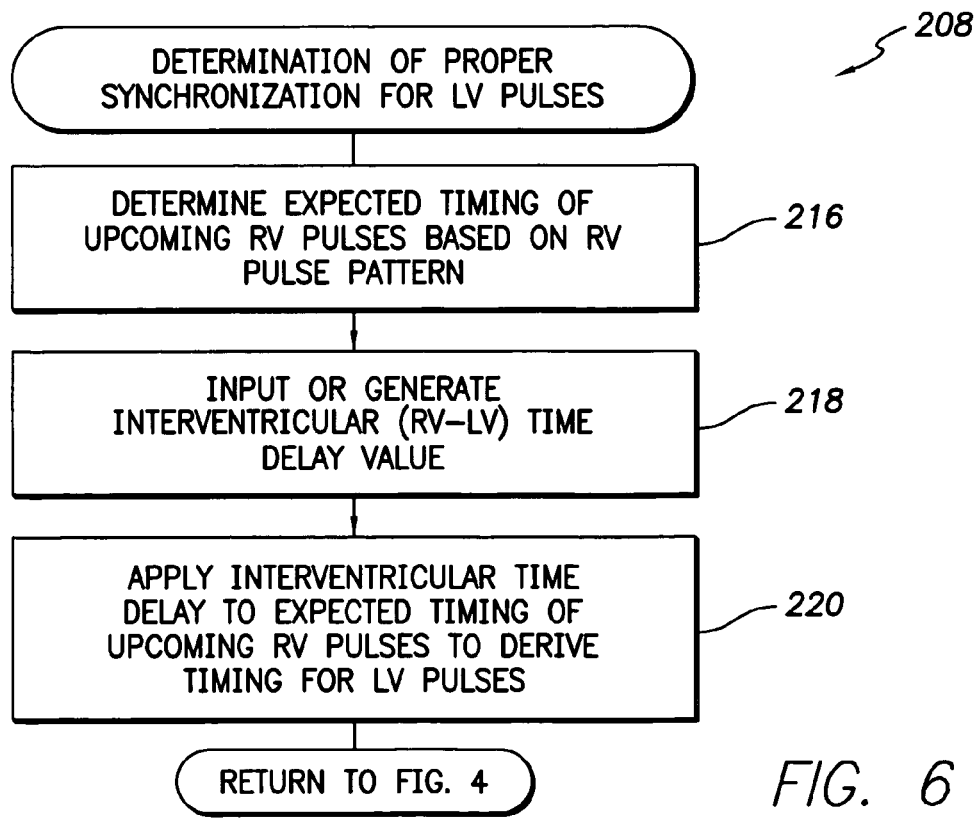
FIG. 6 is a flow diagram providing an exemplary technique for synchronizing supplemental pacing pulses to the timing sequence of the primary pulses for use with the technique of FIG. 4.

With reference to FIG. 6, exemplary techniques for determining the synchronization of LV pacing pulses for use at step 208 of FIG. 4 will now be described. This technique assumes that the timing pattern of the RV pulses as already been determined. At step 216, the synchronization controller of the satellite pacer determines the expected timing of one or more additional RV pulses based upon the RV pulse pattern, e.g. the synchronization controller determines the precise time when the next RV pulse is expected. For the case where the RV pacing rate is constant, the expected time for additional RV pulses is determined based on the inter-pulse interval applied to the last RV pulse time. For the case where the RV pacing rate is changing, but in a linear fashion, the expected timing of additional RV pulses is determined by extrapolating the same rate of change into the future. In circumstances where a more complicated timing pattern is being employed by the primary pacer/ICD, the satellite pacer uses that pattern in conjunction with the times of RV pulses already detected to determine the expected times of upcoming primary pulses. In any case, at step 218, a predetermined interventricular RV-LV time delay value is input from memory or otherwise generated. This value may be initially specified by, for example, a physician or other medical professional, then programmed into the satellite pacer using an external programming device.

Depending upon the implementation, the interventricular delay may vary according to the ventricular rate and so the synchronization controller may need to automatically adjust the RV-LV rate based on the RV rate. In any case, at step 220, the synchronization controller then applies the current value of the interventricular time delay to the expected timing of the next RV pulse to derive the timing for the next LV pulse. Hence, if the RV-LV delay is positive, the synchronization controller adds the interventricular delay to the time value of the next expected to RV pulse so that the next LV pulse will be delivered after that RV pulse, but subject to the interventricular delay. On the other hand, if the RV-LV delay is negative, the synchronization controller subtracts and the delay amount from the time value of the next expected RV pulse so that the next LV pulse will be delivered prior to that RV pulse, but again subject to the specified interventricular delay. Finally, if an interventricular delay of zero specified, then the satellite pacer merely uses the same timing of the next expected RV pulse for delivering the next LV pulse. Once the timing for one or more upcoming LV pulses has been determined, processing returns to FIG. 4.

Thus, FIGS. 4-6 illustrate general techniques for determining the timing pattern of RV pulses delivered by a primary pacing device. Principles may be applied to pacing pulses delivered by a primary pacing device to other chambers of the heart as well, not just RV pulses. Moreover, in many implementations, simpler synchronization techniques may be sufficient. For example, for patients who are paced primarily at only a constant rate, such as at a base rate, it may be sufficient to provide a satellite device capable of just tracking a constant rate. In this regard, many patients are paced 99% of the time at base rate. Thus, although their primary pacer may be capable of more sophisticated pacing, it is rarely used. Hence, for such patients, it is typically sufficient to provide a satellite pacer capable of just tracking a constant rate. During the relatively brief periods of time when the primary pacer is not pacing at a constant rate, the satellite device merely suspends satellite pacing, then resumes once a constant rate is reestablished. More sophisticated devices and techniques have been described herein, in part, for the sake of completeness. As can be appreciated, the satellite device can be designed and configured in accordance with a wide range of implementations for use with a wide range of primary pacing devices. Also for the sake of completeness, a detailed description of exemplary primary pacer/ICD and satellite pacing devices for use with the system of FIG. 1 will now be provided. The techniques of the invention, however, may be performed using any suitable implantable components.

FIG. 7 illustrates a primary pacing device 10 in electrical communication with heart 312 by way of three leads 320 and 330 suitable for delivering multi-chamber stimulation and shock therapy. To sense atrial cardiac signals and to provide right atrial chamber stimulation therapy, primary pacing device 10 is coupled to an implantable right atrial lead 320 having at least an atrial tip electrode 322, which typically is implanted in the right atrial appendage. The primary pacing device 10 is also shown in electrical communication with the heart by way of an implantable RV lead 330 having, in this embodiment, a RV tip electrode 332, a RV ring electrode 334, a RV (RV) coil electrode 336, and an SVC coil electrode 338. Typically, RV lead 330 is transvenously inserted into the heart so as to place the RV tip electrode 332 in the RV apex so that the RV coil electrode 336 will be positioned in the right ventricle and the SVC coil electrode 338 will be positioned in the superior vena cava. Accordingly, the RV lead 330 is capable of receiving cardiac signals as well as delivering stimulation in the form of pacing and shock therapy to the right ventricle.

Figure 8:
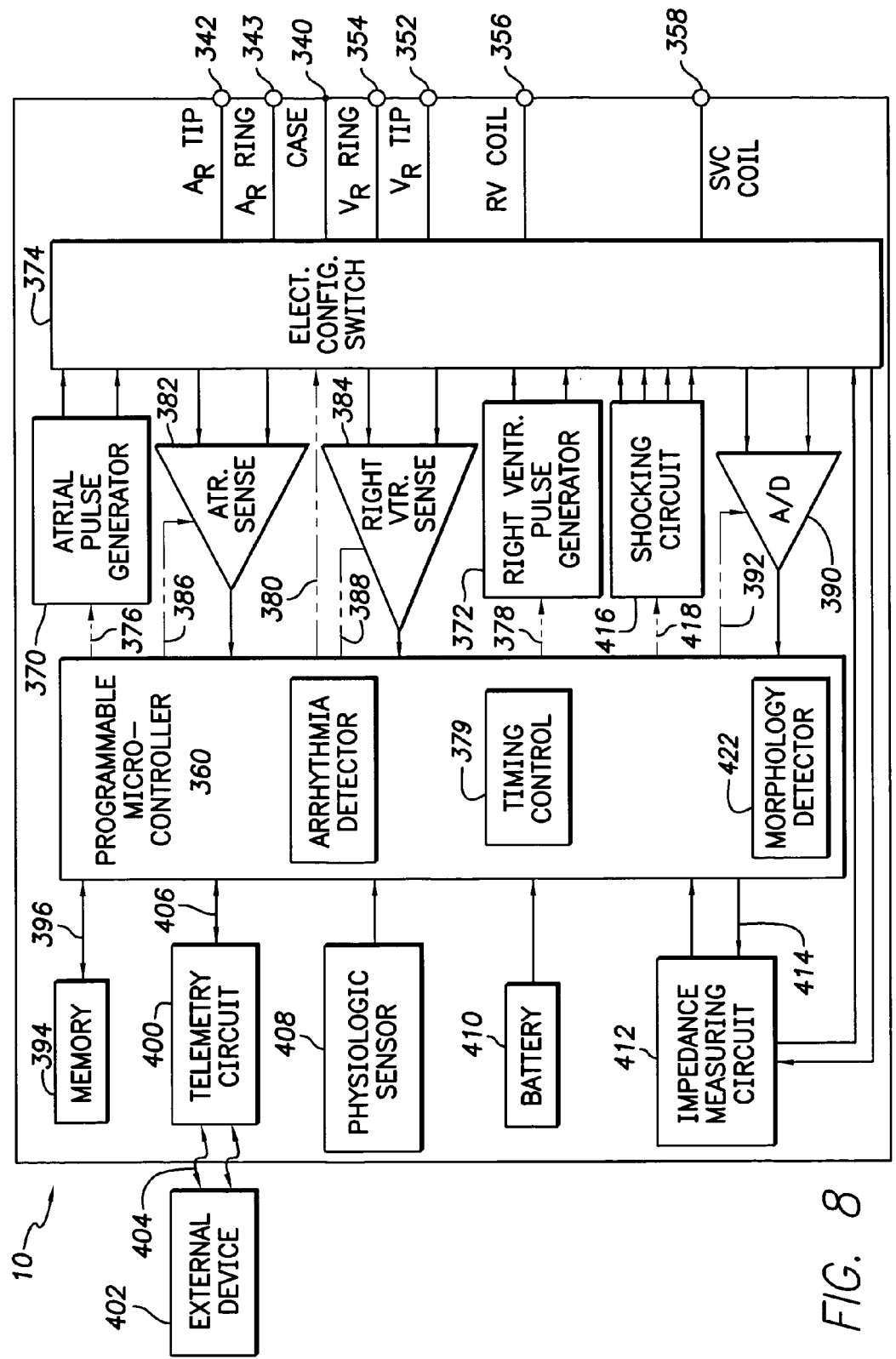
FIG. 8 is a functional block diagram of pertinent components of the primary pacing device of FIG. 7.

FIG. 8 illustrates a simplified block diagram of primary pacing device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and/or pacing stimulation.

Primary pacing device 10 includes a housing 340 which is often referred to as a "can", "case" or "case electrode", and which may be programmably selected to act as the return electrode for all "unipolar" modes. The housing 340 may further be used as a return electrode alone or in combination with one or more of the coil electrodes 336 or 338, for shocking purposes. The housing 340 further includes a connector (not shown) having a plurality of terminals, 342, 343, 352, 354, 356, and 358 (shown schematically and, for convenience, the names of the electrodes to which they are connected are shown next to the terminals). As such, to achieve right atrial sensing and pacing, the connector includes at least a right atrial tip terminal 342 adapted for connection to the right atrial ($A_R$) tip electrode 322. To support right chamber sensing, pacing and/or shocking, the connector further includes a RV ($V_R$) tip terminal 352, a RV ($V_R$) ring terminal 354, a RV shocking terminal (coil) 356, and an SVC shocking terminal (coil) 358, which are adapted for connection to the RV tip electrode 332, RV ring electrode 334, the RV coil electrode 336, and the SVC coil electrode 338, respectively.

At the core of primary pacing device 10 is a programmable microcontroller 360 that controls the various modes of stimulation therapy. The microcontroller 360 typically includes a microprocessor, or equivalent control circuitry or processor, designed specifically for controlling the delivery of stimulation therapy, and may further include RAM or ROM memory, logic and timing circuitry, state machine circuitry, and I/O circuitry. Typically, microcontroller 360 includes the ability to process or monitor input signals (data) as controlled by program code stored in a designated block of memory. The details of the design and operation of microcontroller 360 are not critical to the present invention. Rather, any suitable microcontroller 360 may be used that carries out the functions described herein. The use of microprocessor-based control circuits for performing timing and data analysis functions is well known in the art.

As shown in FIG. 8, an atrial pulse generator 370 and a ventricular pulse generator 372 generate pacing stimulation pulses for delivery by the right atrial lead 320 and/or the RV lead 330 via a switch bank 374. It is understood that in order to provide stimulation therapy in the various chambers of the heart, the atrial pulse generator 370 and the ventricular pulse generator 372 may include dedicated, independent pulse generators, multiplexed pulse generators, or shared pulse generators. The atrial pulse generator 370 and the ventricular pulse generator 372 are controlled by the microcontroller 360 via appropriate control signals 376 and 378, respectively, to trigger or inhibit the stimulation pulses. The microcontroller 360 further includes timing control circuitry 379 which is used to control the timing of such stimulation pulses (e.g., pacing rate, atrio-ventricular (AV) delay, atrial interconduction (A-A) delay, pacing mode, etc.), as well as to keep track of the timing of refractory periods, PVARP intervals, noise detection windows, evoked response windows, alert intervals, marker channel timing, etc. The switch bank 374 includes a plurality of switches for connecting the desired electrodes to the appropriate I/O circuits, thereby providing complete electrode programmability. Accordingly, the switch bank 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320 and the RV lead 330, through the switch bank 374, for detecting the presence of cardiac activity in the heart. Accordingly, the atrial and ventricular sensing circuits 382 and 384 may include dedicated sense amplifiers, multiplexed amplifiers, or shared amplifiers. The switch bank 374 determines the "sensing polarity" of the cardiac signal by selectively closing the appropriate switches. In this way, the clinician may program the sensing polarity independent of the stimulation polarity. Each of the sensing circuits, 382 and 384, preferably employ one or more low power, precision amplifiers with programmable gain and/or automatic gain control, bandpass filtering, and a threshold detection circuit, to selectively sense the cardiac signal of interest. The automatic gain control enables the primary pacing device 10 to deal effectively with the difficult problem of sensing the low amplitude signal characteristics of atrial or ventricular fibrillation.

The outputs of the atrial and ventricular sensing circuits 382 and 384 are connected to the microcontroller 360 for triggering or inhibiting the atrial and ventricular pulse generators 370 and 372, respectively, in a demand fashion, in response to the absence or presence of cardiac activity, respectively, in the appropriate chambers of the heart. The atrial and ventricular sensing circuits 382 and 384, in turn, receive control signals over signal lines 386 and 388 from the microcontroller 360, for controlling the gain, threshold, polarization charge removal circuitry (not shown), and the timing of any blocking circuitry (not shown) coupled to the inputs of the atrial and ventricular sensing circuits 382 and 384.

For arrhythmia detection, primary pacing device 10 utilizes the atrial and ventricular sensing circuits 382 and 384 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Note that, strictly speaking, P-waves, R-waves and T-waves are features of the surface EKG. For convenience, herein, the terms P-wave, R-wave and T-wave are used to refer to the corresponding internal signal component.

Cardiac signals are also applied to the inputs of an analog-to-digital (A/D) data acquisition system 390. The data acquisition system 390 is configured to acquire intracardiac electrogram signals, convert the raw analog data into digital signals, and store the digital signals for later processing and/or telemetric transmission to an external device 402. The data acquisition system 390 is coupled to the right atrial lead 320 and the RV lead 330 through the switch bank 374 to sample cardiac signals across any pair of desired electrodes. Advantageously, the data acquisition system 390 may be coupled to the microcontroller 360 or other detection circuitry, for detecting an evoked response from the heart 312 in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 360 detects a depolarization signal during a window following a stimulation pulse, the presence of which indicates that capture has occurred. Microcontroller 360 enables capture detection by triggering the ventricular pulse generator 372 to generate a stimulation pulse, starting a capture detection window using the timing circuitry within the microcontroller 360, and enabling the data acquisition system 390 via control signal 392 to sample the cardiac signal that falls in the capture detection window and, based on the amplitude of the sampled cardiac signal, determines if capture has occurred.

Microcontroller 360 is further coupled to a memory 394 by a suitable data/address bus 396, where the programmable operating parameters used by the microcontroller 360 are stored and modified, as required, in order to customize the operation of the primary pacing device 10 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the heart within each respective tier of therapy. A feature of the primary pacing device 10 is the ability to sense and store a relatively large amount of data (e.g., from the data acquisition system 390), which data may then be used for subsequent analysis to guide the programming of the primary pacing device 10.

Advantageously, the operating parameters of the primary pacing device 10 may be non-invasively programmed into the memory 394 through a telemetry circuit 400 in telemetric communication with the external device 402, such as a programmer, transtelephonic transceiver, or a diagnostic system analyzer. The telemetry circuit 400 is activated by the microcontroller 360 by a control signal 406. The telemetry circuit 400 advantageously allows intracardiac electrograms and status information relating to the operation of the primary pacing device 10 (as contained in the microcontroller 360 or memory 394) to be sent to the external device 402 through an established communication link 404.

In the preferred embodiment, the primary pacing device 10 further includes a physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states). Accordingly, the microcontroller 360 responds by adjusting the various pacing parameters (such as rate, AV Delay, etc.) at which the atrial and ventricular pulse generators, 370 and 372, generate stimulation pulses.

The primary pacing device 10 additionally includes a power source such as a battery 410 that provides operating power to all the circuits shown in FIG. 8. For the primary pacing device 10, which employs shocking therapy, the battery 410 is capable of operating at low current drains for long periods of time and also be capable of providing high-current pulses (for capacitor charging) when the patient requires a shock pulse. The battery 410 should preferably have a predictable discharge characteristic so that elective replacement time can be detected. Accordingly, the primary pacing device 10 can employ lithium/silver vanadium oxide batteries or any other appropriate power source.

The primary pacing device 10 further includes a magnet detection circuitry (not shown), coupled to the microcontroller 360. The purpose of the magnet detection circuitry is to detect when a magnet is placed over the primary pacing device 40, which magnet may be used by a clinician to perform various test functions of the primary pacing device 10 and/or to signal the microcontroller 360 that an external programmer 402 is in place to receive or transmit data to the microcontroller 360 through the telemetry circuit 400.

As further shown in FIG. 8, the primary pacing device 10 is shown as having an impedance measuring circuit 412, which is enabled by the microcontroller 360 via a control signal 414. Certain applications for an impedance measuring circuit 412 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 412 is advantageously coupled to the switch bank 374 so that any desired electrode may be used.

It is a primary function of the primary pacing device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules), or high (11-40 joules) energy, as controlled by the microcontroller 360. Such shocking pulses are applied to the heart through at least two shocking electrodes, as shown in this embodiment, selected from the RV coil electrode 336 and/or the SVC coil electrode 338 (FIG. 7). As noted above, the housing 340 may act as an active electrode in combination with the RV electrode 336, or as part of a split electrical vector using the SVC coil electrode 338 (e.g., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of 5-40 joules), delivered asynchronously (since R-waves may be too disorganized) and pertaining exclusively to the treatment of fibrillation. Accordingly, the microcontroller 360 is capable of controlling the synchronous or asynchronous delivery of the shocking pulses.

Figure 9:
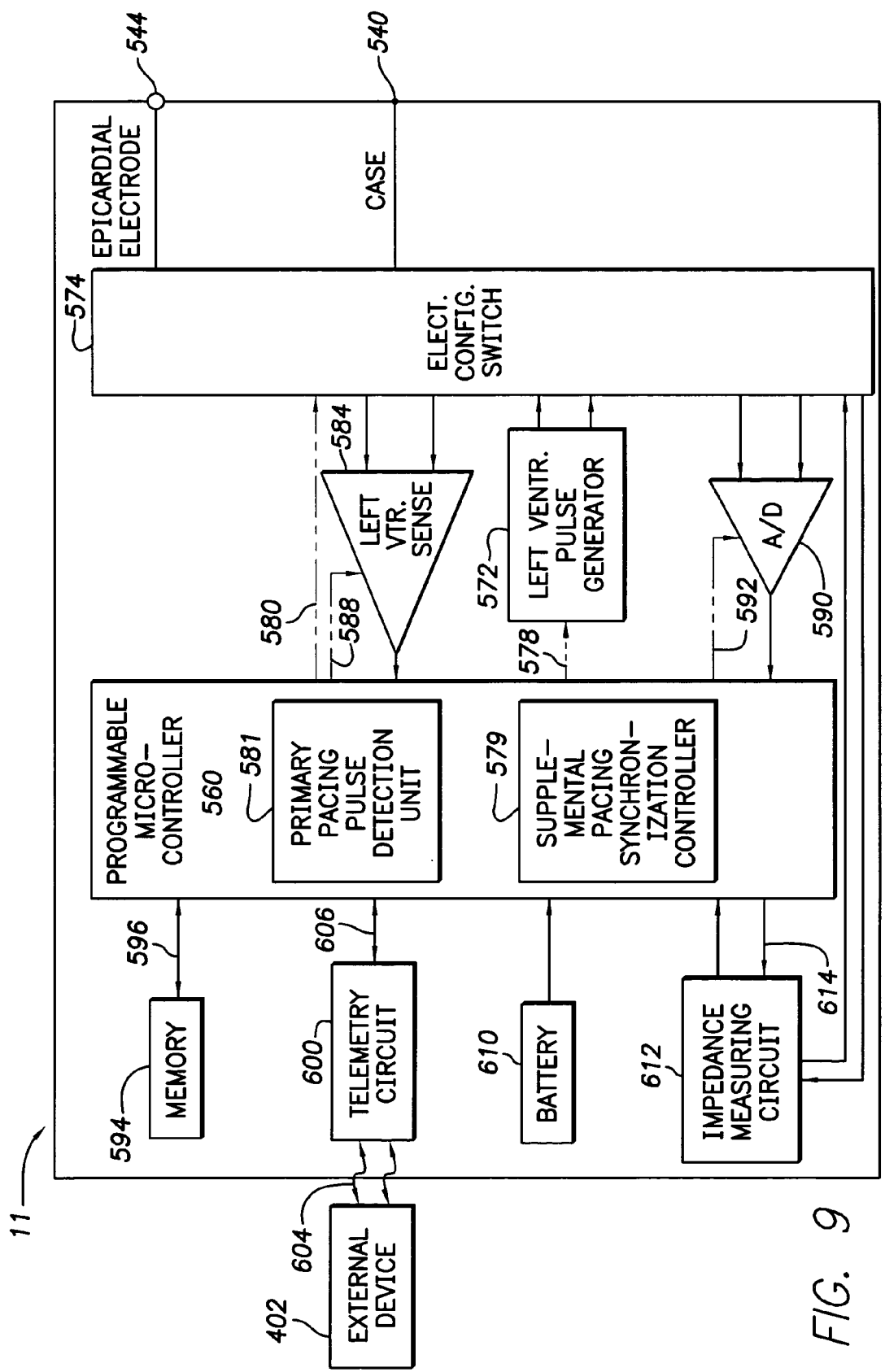
FIG. 9 is a functional block diagram of pertinent components of the satellite pacing device of FIG. 7, particularly components for automatically determining a timing pattern of primary pulses delivered by the primary device of FIG. 8.

FIG. 9 is a simplified block diagram of satellite pacing device 11, which is capable, at least, of detecting primary (i.e. RV) pacing pulses in the heart and for selectively providing supplemental (i.e. LV) pacing pulses to the left ventricles synchronized with the primary pulses. Many of the components of the satellite device are the same or similar to corresponding components of the primary device and so will not be described again in any detail. As with the primary device, the particular satellite device shown herein is provided for illustration purposes only, and one of skill in the art could readily duplicate, eliminate or disable the appropriate circuitry in any desired combination. The housing 540 for the satellite device 11, shown schematically in FIG. 9, is referred to herein as the "satellite can", "satellite case" or "satellite case electrode" and may be programmably selected to act as the return electrode for any "unipolar" satellite pacing modes. Housing 540 further includes a connector (not shown) having a terminal 544 (shown schematically). As such, to achieve LV sensing and pacing, the connector includes at least a LV epicardial electrode terminal 544, adapted for connection to the LV epicardial electrode 15 of FIG. 7, respectively. In other implementations, a lead having separate tip and ring epicardial electrodes may be employed. If so, separate tip and ring electrode terminals are provided. Additional terminals may be provided for use with additional leads to allow, for example, pacing at multiple epicardial sites.

Satellite device 11 includes a programmable microcontroller 560, which controls the various modes of stimulation therapy. As with the primary stimulation device, details of the design and operation of the microcontroller of the satellite device are not critical to the invention and any suitable microcontroller may be used that carries out the functions described herein. A LV pulse generator 572 generates pacing stimulation pulses for delivery to the epicardial lead via an electrode configuration switch 574. In order to provide stimulation therapy to left ventricle, ventricular pulse generator 572 may include dedicated, independent pulse generators, multiplexed pulse generators, or shared pulse generators. Pulse generator 572 is controlled by microcontroller 560 via appropriate control signals 578 to trigger or inhibit the stimulation pulses.

Microcontroller 560 further includes a supplemental pacing synchronization controller 579 for controlling the timing of such stimulation pulses in accordance with the techniques described above. Switch 574 includes switches for connecting the electrodes to the appropriate I/O circuits. For example, switch 574, in response to a control signal 580 from microcontroller 560, determines the polarity of stimulation pulses (e.g., unipolar, bipolar, combipolar, etc.) by selectively closing the appropriate combination of switches (not shown) as is otherwise known in the art. Ventricular sensing circuit 584 may also be selectively coupled to the LV epicardial lead 13, through switch 574 for sensing primary pacing pulses generated by the primary pacing device. The LV sensing circuit 584 may include dedicated sense amplifiers, multiplexed amplifiers, or shared amplifiers. Switch 574 determines the "sensing polarity" of the LV epicardial signal by selectively closing the appropriate switches, as is also known in the art. In this way, the clinician may program the sensing polarity independent of the stimulation polarity. Sensing circuit 584 preferably employs one or more low power, precision amplifiers with programmable gain and/or automatic gain control, band-pass filtering, and a threshold detection circuit, as known in the art, to selectively sense the primary pacing pulses. The outputs of ventricular sensing circuit 584 are connected to microcontroller 560 which, in turn, are able to trigger or inhibit ventricular pulse generator 572 in a demand fashion in response to the absence or presence of primary pacing pulses. Depending upon the implementation, the satellite device may be configured to perform arrhythmia detection. If so, satellite device 11 utilizes ventricular sensing circuit 584 to sense cardiac signals via the epicardial lead to determine whether a rhythm is physiologic or pathologic.

The microcontroller also includes a primary pacing pulse detection unit 581, which processes signals received via sense amplifier 584 to identify primary pacing pulses therein. Information pertaining to the primary pacing pulses is forwarded to the aforementioned pacing synchronization controller 579 so that the synchronization controller can determine the timing pattern of the primary pulses and further specify the timing pattern for delivering supplemental pacing pulses in synchronization with upcoming primary pacing pulses.

Cardiac signals are also applied to the inputs of an analog-to-digital (A/D) data acquisition system 590. The data acquisition system 590 is configured to acquire LV epicardial electrogram signals, convert the raw analog data into a digital signal, and store the digital signals for later processing and/or telemetric transmission to external device 402. Data acquisition system 590 is coupled to the LV epicardial lead 13 through switch 574 to sample signals. Microcontroller 560 is further coupled to a memory 594 by a suitable data/address bus 596, wherein the programmable operating parameters used by microcontroller 560 are stored and modified, as required, in order to customize the operation of satellite pacing device 510 to suit the needs of a particular patient. Such operating parameters define, for example, pacing pulse amplitude, pulse duration, electrode polarity, sensitivity, automatic features, and any arrhythmia detection criteria. Advantageously, the operating parameters of satellite device 11 may be non-invasively programmed into memory 594 through telemetry circuit 600 in telemetric communication with external device 402. Telemetry circuit 600 is activated by the microcontroller by a control signal 606. Telemetry circuit 600 advantageously allows electrograms and status information relating to the operation of the satellite device (as contained in the microcontroller 560 or memory 594) to be sent to the external device through an established communication link 604. The satellite stimulation device additionally includes a battery 610, which provides operating power to all of the components shown in FIG. 9. Satellite device 11 may also include an impedance measuring circuit 612, which is enabled by the microcontroller 660 via a control signal 614 for verifying that the LV epicardial lead is function properly.

Pulse Encoding/Decoding Communication Techniques

Referring now to FIGS. 10-16, techniques for communicating information from one implanted medical device to another via encoded therapeutic pulses will be described. FIG. 1 provide as an overview of the technique. Initially, at step 700, a primary implantable medical stimulation device, such as a primary cardiac pacer, generates a therapeutic electrical stimulation pulse encoded with information to be communicated to a secondary implantable medical stimulation device, such as a satellite cardiac pacer. At step 702, the encoded therapeutic stimulation pulse is delivered to patient tissue, such as patient heart tissue. At step 704, the satellite pacer detects the therapeutic stimulation pulse within tissues of the patient and, at step 706, decodes the detected pulse to extract the encoded information.

In one example, the primary stimulation device encodes information pertaining to a timing pattern of upcoming primary pulses so that the secondary device can then synchronize its supplemental stimulation pulses with the upcoming primary pulses. By synchronization, it is again meant that the supplemental pulses are delivered at a specified time a relative to the primary pulses, which may be either before, during, or after corresponding primary pacing pulses. In this manner, the timing pattern of the primary pulses is conveyed to the secondary device without requiring any information to be transmitted directly from the primary device to the secondary device via conventional wireless or (wireline) telemetry.

Figure 11:
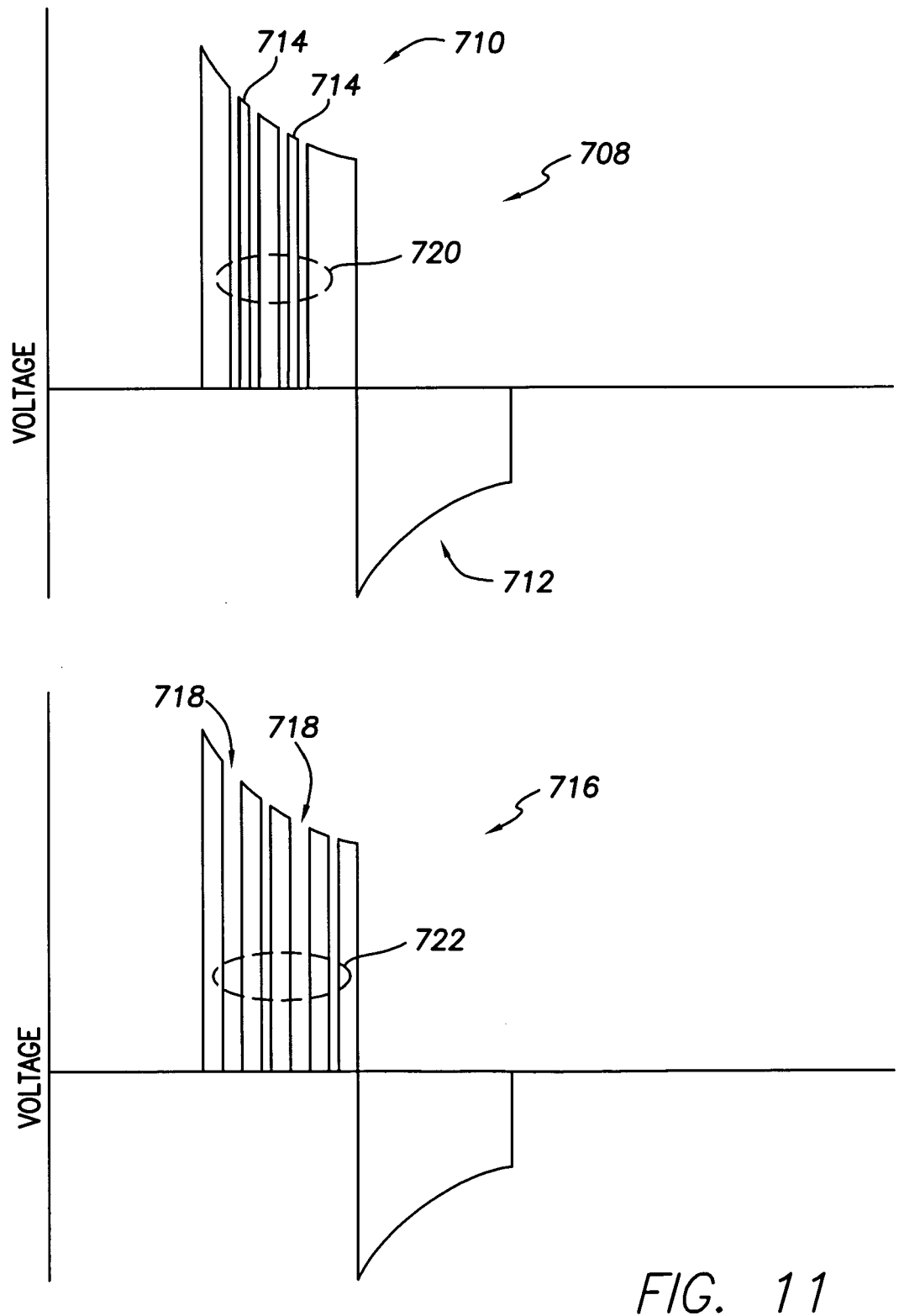
FIG. 11 provides stylized diagrams of exemplary modulated pacing pulse delivered using the technique of FIG. 10.

Exemplary encoded pulses are illustrated in FIG. 11 for an example wherein the pulses are biphasic cardiac pacing pulses. Within a first graph of FIG. 11, a first exemplary a biphasic primary pacing pulse 708 is illustrated, which includes a first, positive phase 710 and a second, negative phase 712. However, the polarity of the phases may be reversed. Each phase illustrates the characteristic exponential decay associated with the discharge of a pulse generation capacitor used to generate a pulse, with the second phase of pulse having a smaller overall magnitude of the first phase. Note that the exemplary pacing pulses of FIG. 3 discussed above did not illustrate this exponential decay since FIG. 3 was merely intended to illustrate a series of discrete pulses and was not intended to illustrate the actual shape of individual pacing pulses. As with the diagrams of FIG. 3, the diagrams of FIG. 11 are merely stylized representations and should not be construed as representing actual clinically detected signals. The horizontal (time) axis and the vertical (magnitude) axis are again both in arbitrary units.

The first phase 710 of pulse 708 is modulated to include a plurality of individual pulse portions 714 each separated by a brief period of zero voltage, which may be produced by selectively and temporarily shunting the output pulse to ground. In the example of pulse 708, the spacing or interval between individual pulse portions is uniform. However, the width of the individual pulse portions differs. The relative width of the pulse portions may be modulated so as to encode information to be communicated from the primary stimulation device to the secondary stimulation device. Otherwise conventional data encoding techniques may be used to encode information based upon the width of the various pulse portions. In one specific example, each individual pulse portion may have one of two possible widths, with the first width being representative of a binary "one" and the second width being representative of a binary "zero." In this manner, the widths of the various individual pulse portions are modulated to represent a digital bit stream. More complex encoding schemes may be employed as well.

A second exemplary primary pulse 716 is also shown in FIG. 11. Within a first phase of pulse 716, individual pulse portions are again provided. However, in this example, the relative spacing 718 between the pulse portions varies, whereas the width of the pulse portions remains constant. The relative widths of the spacing between the pulse portions may be modulated to encode information, again using otherwise conventional encoding techniques. In a specific example, each individual interval may have one of two possible widths, representative of binary "ones" and "zeroes", respectively, so as to encode a portion of a digital bit stream. More complex encoding schemes may again be employed.

Although examples are illustrated in FIG. 11 wherein the intervals have zero voltage, this is not necessary. It is sufficient that the intervals simply have a voltage or some other characteristic that is detectably different from the non-interval portions of the pulse. Indeed, each interval may be controlled to have a potentially different voltage level, wherein information is encoded based on the specific voltages of the individual intervals. As can be appreciated, a wide variety of techniques may be employed to encode information within a therapeutic pulse and no attempt is made here to describe all possible techniques.

Typically, the overall duration of the pulse is in the range of 0.2-2.0 ms. Individual pulse portions and/or the intervals therebetween may have, e.g., durations in the range of 15-30 μseconds. As such, the individual pulse portions/intervals are substantially shorter than the duration of the overall pulse. In FIG. 11, the width of the individual pulse portions/intervals is exaggerated compared to the width of the overall pulse so that the individual pulse portions/intervals may be more clearly viewed. By using intervals that are substantially shorter than the overall pulse duration, the presence of the intervals thereby does not affect the ability of the pulse to deliver therapy. In the case of cardiac pacing pulses, for example, the presence of a sequence of short intervals of zero voltage does not affect the ability of the pacing pulse to depolarize the myocardial tissue. Also note that, depending on the implementation, only a portion of the pulse may be used to encode information. For example, only the middle portion of the first phase of pulse may be used to encode information. In other examples, information is encoded within a portion of the second phase of pulse. In still other examples, both phases of the pulse are used to encode information. Within pulse 708, the portion of the pulse used to encode information is identified by reference numeral 720. Within pulse 716, the portion of the pulse used to encode information is identified by reference numeral 722. Only a few exemplary pulse portions/intervals are shown. In practice, the pulse may be modulated to provide far more individual pulse portions/intervals so as to communicate a greater amount of information.

A wide variety of types of information may be communicated from the primary device to the secondary device using encoded pacing pulses. In one example, the encoded information specifies the timing pattern of upcoming primary pacing pulses so that the secondary device may synchronize its pacing pulses with upcoming primary pulses. Preferably, though, not all pacing pulses are encoded with information. Rather, most pacing pulses are otherwise conventional. Only in circumstances where the primary device needs to convey information to the secondary device is a pulse modulated to encode information.

In a simple case where the primary device delivers pacing pulses at a fixed rate, only a single primary pulse may be encoded with information specifying the current pacing rate and the secondary device can use that information to synchronize its pulses. If the primary device needs to change the fixed pacing rate, another primary pulse is encoded with information specifying the new pacing rate so that the secondary device may then change the rate at which secondary pulses are delivered so as to remain synchronized with the primary pulses. As can be appreciated, with fixed pacing, it is only necessary to communicate information to the secondary device in circumstances where the rate is due to change. Hence, it is only necessary to encode information within primary pacing pulses just prior to a rate change. However, if preferred, each individual pulse may be encoded with the pacing rate. This redundancy helps ensure that the secondary device will not miss or overlook a rate change.

If the primary device employs a more sophisticated pacing scheme, such as one in which the intervals of between primary pacing pulses vary from pulse to pulse, then primary pacing pulses are preferably encoded with information specifying the more sophisticated pacing scheme. For example, individual primary pacing pulse may be encoded with information representative of upcoming variations in primary pacing pulse intervals, such information specifying predetermined gradual increases or decreases in pacing rate.

In some circumstances, it is desirable that each individual pulse simply be encoded to specify when the next primary pulse will be delivered. This is particularly useful in circumstances where the primary device operates to increase heart rate variability by changing the interval between each successive pair of primary pacing pulses more or less at random, such that there is no predetermined "pattern" for upcoming pacing pulses. So long as the primary device can at least specify when the next primary pulse is to be delivered, the secondary device can synchronize its next pulse to the next primary pulse, even in the absence of any predetermined pacing pattern. This represents one important advantage of the communication technique of FIGS. 9-16 over the pattern detection technique of FIGS. 1-9, which relies on the presence of a detectable pattern. Also, even in circumstances where a predetermined pattern is employed by the primary device, the communication technique of FIGS. 9-16 allows the secondary device to be immediately advised to any changes in the pattern so that it can promptly adjusting the timing of its pulses. With the pattern detection technique of FIGS. 1-9, there can be some delay before a new pacing pattern is recognized by the secondary device.

Hence, information pertaining to the delivery of upcoming primary pacing pulses may be communicated from the primary device to the secondary device, from which the secondary device determines the appropriate time for delivery of upcoming secondary pacing pulse. Additionally, however, other types of information may be communicated from the primary device to the second or device as well. For example, the primary device may communicate information to the secondary device specifying the manner by which the secondary device is to synchronize its pacing pulses with the primary pulses. In circumstances wherein the primary and secondary devices operate to provide RV/LV CRT, the primary device may communicate information to the secondary device specifying the interventricular delay interval to be used, i.e. the precise value of RV-LV delay, which, as noted, may have a positive value, a negative value, or may be set to zero. If negative, the satellite pacer delivers its pulse shortly before the next expected primary pulse. If positive, the satellite pacer delivers its pulse shortly following the next primary pulse. If the interventricular delay set to zero, the secondary pulses are generated substantially simultaneous with the corresponding expected primary pulses.

Other types of control information may be communicated as well. For example, the primary device may activate or deactivate the secondary device by encoding appropriate activation/deactivation commands within the primary pulses. As can be appreciated, a wide variety of command or control information may be communicated from the primary device to secondary device. In one specific example, wherein the primary pacer activates the secondary pacer using an encoded command, the primary pacer is configured to then sense pacing pulses delivered by the secondary pacing pacer to verify that secondary pacing has in fact been activated. Depending on the implementation, the secondary device may be equipped to encode information within its pacing pulses that provides an acknowledgment to the primary device of receipt of any communicated information. In such implementations, the primary device is equipped with the capability to detect and decode any acknowledgement information encoded within secondary pacing pulses. In other words, both the primary and secondary devices can be equipped for encoding and decoding information via modulated pacing pulses, so as to provide communication back-and-forth between the two devices. If more than two implantable devices are provided, any or all of the devices may be equipped for the encoding and decoding of information via modulated therapeutic stimulation pulses.

Figure 10:
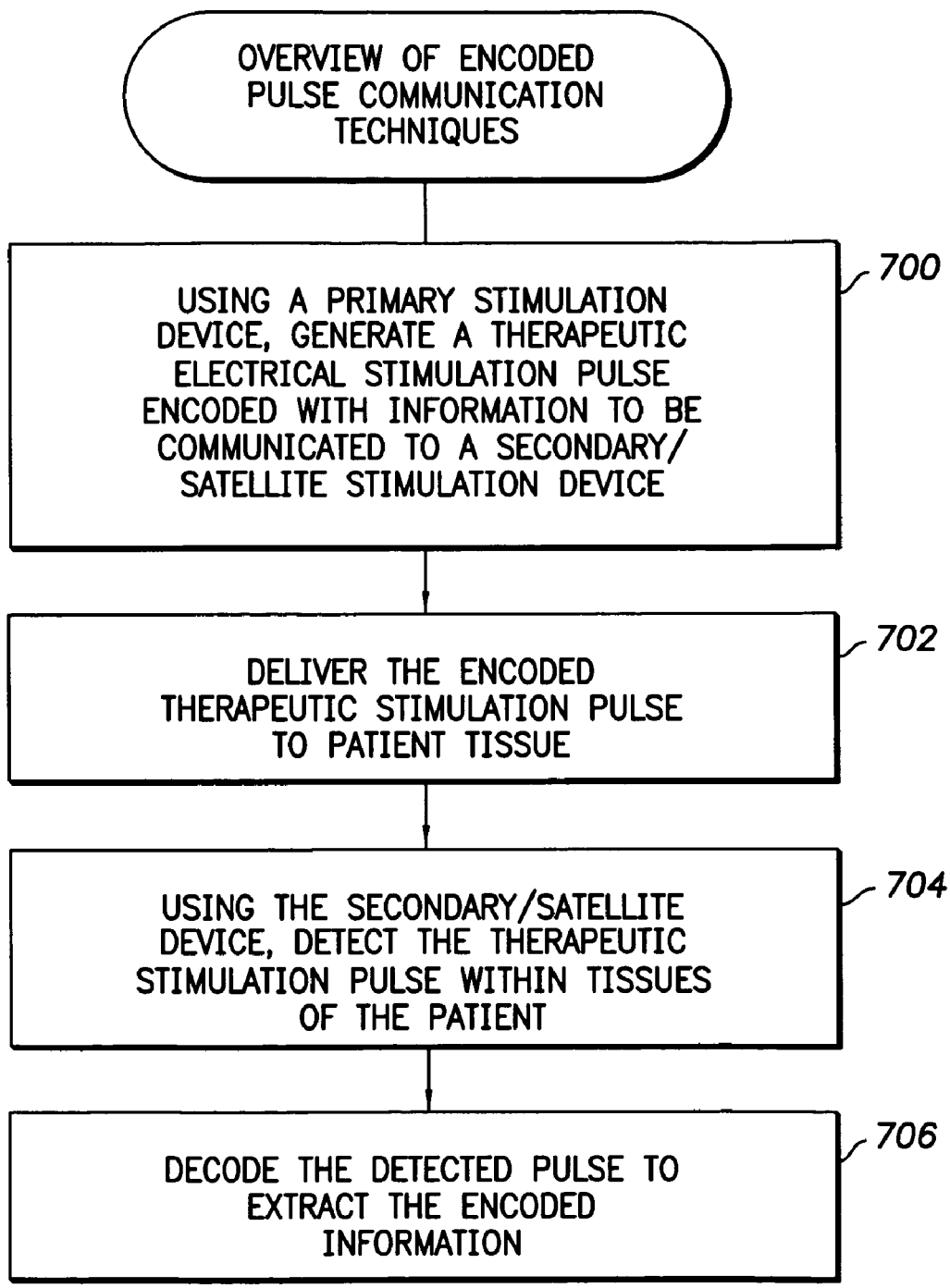
FIG. 10 is a flow diagram providing an overview of a second exemplary technique for delivering pacing therapy using the system of FIG. 1, wherein the primary pacing device communicates timing information to the secondary device via encoded therapeutic pacing pulses.

Hence, using the techniques of FIGS. 10-11, any of a wide variety of information may be communicated among various implantable devices capable of sensing and/or delivering therapeutic stimulation pulses. In some cases, depending upon the amount of information to be conveyed, information may be encoded within two or more consecutive stimulation pulses. With reference to the following figures, specific examples for use in communication information in connection with performing CRT will now be described.

Figure 12:
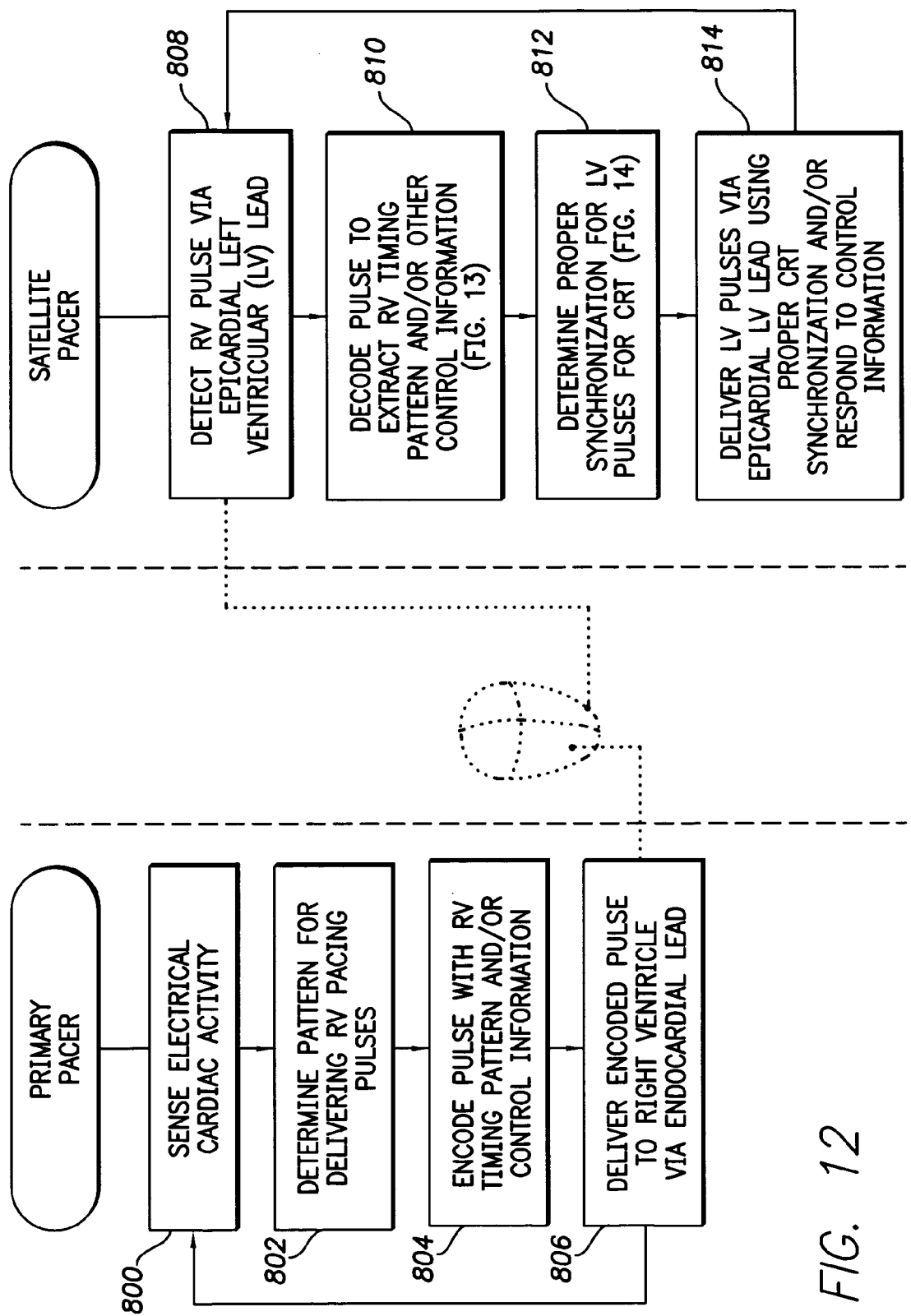
FIG. 12 is a flow diagram illustrating an exemplary technique provided in accordance with the general technique of FIG. 10, particularly for use with a primary pacer equipped to pace the RV using an endocardial lead and a secondary pacer equipped to pace the LV using an epicardial lead.

FIG. 12 provides an overview of steps performed by a primary pacer and a satellite pacer for an implementation directed primarily to delivering CRT. Steps performed by the primary pacer are shown on the left. Steps performed by the satellite pacer are shown on the right. A stylized representation of a heart is provided within the figure to illustrate that information is communicated from the primary pacer to the satellite pacer via pulses delivered to heart tissue. At step 800, the primary pacer senses electrical cardiac activity using its RV lead then, at step 802, determines a pattern for delivering pacing pulses to the RV. This pattern may be as simple as a fixed RV pacing rate or may involve a much more complicated pacing scheme, such as an antiarrhythmic pacing regime. In other cases, the pacing pattern merely specifies the interval between a current RV pulse being delivered and the next RV pulse to be delivered.

At step 804, the primary pacer modulates one or more RV pacing pulses to encode information pertaining to the pacing pattern or to encode other control information such as the interventricular delay. The specific information to be encoded depends on the information that needs to be communicated to the satellite pacer. For example, if RV fixed rate pacing is being performed, the encoded information may merely represent the fixed RV pacing rate. If variable rate RV pacing is being performed, the encoded information may represent the rate of change of the RV rate. If RV pacing is to be suspended, the pulse is preferably encoded with control information instructing the satellite pacer to deactivate LV pacing. If RV pacing is to be reactivated, the pulse is preferably encoded with control information instructing the satellite pacer to reactivate LV pacing, as well as information specifying the pattern of upcoming RV pulses. At step 806, the primary pacer delivers the encoded RV pacing pulse to the heart of the patient via the RV lead.

Meanwhile, at step 808, the satellite pacer detects of the RV pulse via its epicardial LV lead and, at step 810, decodes the encoded information within the pulse to, e.g. decode the timing pattern of upcoming RV pulses. Exemplary techniques are summarized to below with reference to FIG. 13. Next, at step 812, the satellite pacer determines the proper synchronization for LV pulses for epicardial delivery to the left ventricle in accordance with CRT techniques. An exemplary technique for determining synchronization is described below with reference to FIG. 14. Then, at step 814, the satellite pacer delivers LV pacing pulses via the epicardial LV lead using the proper CRT synchronization so as to improve the cardiac function of the patient.

The steps performed by the primary pacer and the steps performed by the satellite pacer are repeated, each in its own loop. While steps 800 to 806 are repeated, the primary pacer selectively activates and deactivates RV pacing while selectively adjusting the RV pacing rate to, for example, respond to various arrhythmias, deliver ventricular overdrive pacing therapy, or pace the ventricles to ensure a certain degree of heart rate variability, etc. One particularly effective ventricular overdrive technique is "dynamic ventricular overdrive" (DVO), which is described in U.S. patent application Ser. No. 10/456,060, to Park et al., entitled "System And Method For Dynamic Ventricular Overdrive Pacing," filed Jun. 6, 2003. One particularly effective technique for maintaining a certain degree of heart rate variability is set forth in U.S. Pat. No. 6,694,188, Kroll, entitled "Dynamic Control of Overdrive Pacing Based on Degree of Randomness within Heart Rate."

Meanwhile, steps 800 to 806 are repeated by the satellite pacer detects, which responds to information encoded within RV pacing pulses so as to automatically adjust the timing of its LV pacing pulses to remain substantially in synch with any RV pulses being delivered. As already noted, if RV pacing is suspended, the satellite pacer likewise suspends delivery of the LV pulses in response to control information received via an encoded pulse. LV pulses are not again delivered until the primary pacer reactivates RV pacing and instructs the satellite pacer to likewise reactivate delivery of supplemental pacing pulses in synchronization therewith.

Figure 13:
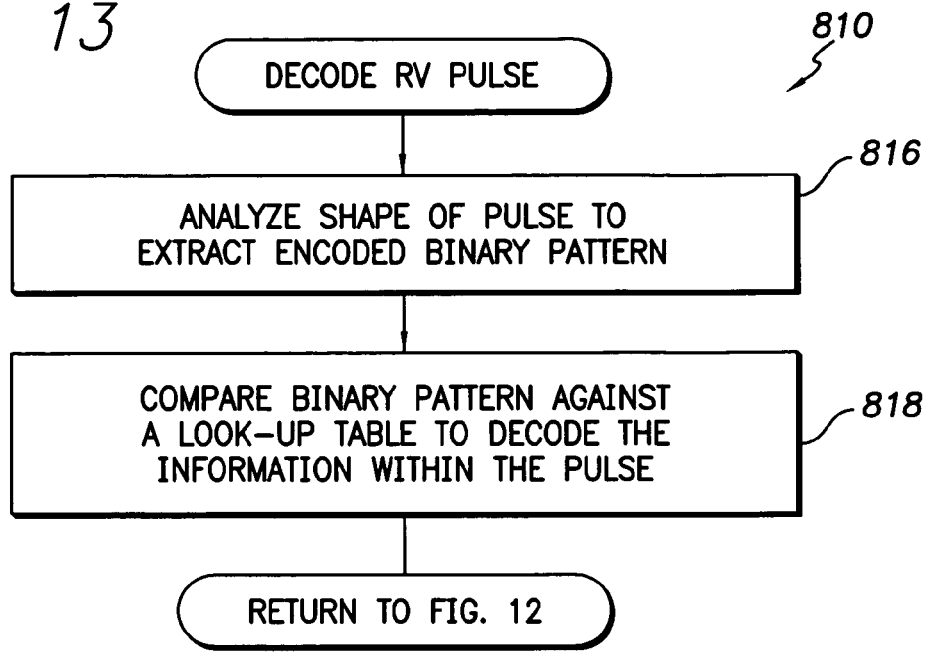
FIG. 13 is a flow diagram providing an exemplary technique for decoding primary RV pulses for use with the technique of FIG. 12.

Turning now to FIG. 13, exemplary techniques for decoding RV pulses will be discussed. Initially, at step 816, a pulse decoder of the satellite pacer analyzes the shape of each RV pacing pulse to determine if any information is encoded therein and, if so, to extract that information. For example, the pulse decoder may be configured to identify the aforementioned pulse portions/intervals within the pulse and to determine their relative widths. The pulse portions/intervals are then converted to a digital pattern or sequence. In a specific example wherein the widths of the pulse portions/intervals encode binary "ones" and "zeroes", the pulse portions/intervals are analyzed and converted into a binary sequence.

The binary sequence is then decoded, at step 818 to determine the timing pattern for upcoming RV pulses or to identify any control codes encoded in the pulse. In one example, the binary sequence is compared against a look-up table providing a list of prestored binary sequences and their predetermined meaning. Some of the prestored sequences may, for example, correspond to specific fixed pacing rates. Others may correspond to specific interventricular delay values. Still others may correspond to control codes, such as activation codes, deactivation codes, etc. In any case, by accessing a look-up table, the satellite pacer can thereby decode the information encoded within pulse.

Typically, most RV pulses generated by the primary pacer are not modulated to include any encoded information. Hence, if no encoded information is found within any particular RV pulse, the satellite pacer simple continues its current pacing scheme. If an encoded binary pattern is found within a pulse but cannot be decoded (perhaps because noise has corrupted the received RV pulse pattern so that it does not correspond to any patterns in the look-up table), the satellite pacer likewise continues its current pacing scheme, with the expectation that the primary pacer will soon detect that the satellite pacer has not responded to the information it has sent and will resend the information via another encoded RV pulse. In implementations wherein the satellite pacer is capable of communicating acknowledgement information back to the primary pacer, the satellite pacer can request that any information not properly received be resent.

With reference to FIG. 13, exemplary techniques for determining the synchronization of LV pacing pulses for use at step 812 of FIG. 12 will now be described. This technique assumes that the timing pattern of upcoming RV pulses as already been received with an encoded RV pulse and has been properly decoded. At step 820, the synchronization controller of the satellite pacer determines the expected timing of one or more additional RV pulses based upon the RV pulse pattern, e.g. the synchronization controller determines the precise time when the next RV pulse will be delivered. For the case where the RV pacing rate is constant, the expected time for additional RV pulses is determined based on the inter-pulse interval applied to the last RV pulse time. For the case where the RV pacing rate is changing, but in a linear fashion, the expected timing of additional RV pulses is determined by extrapolating the same rate of change into the future. In circumstances where a more complicated timing pattern is being employed by the primary pacer/ICD, the satellite pacer uses that pattern in conjunction with the times of RV pulses already detected to determine the expected times of upcoming primary pulses. In any case, at step 822, an interventricular RV-LV time delay value is accessed, i.e. it is input from memory or otherwise generated. If the primary pacer specifies the RV-LV time delay value, this information is extracted by the satellite pacer from an encoded RV pulse and then stored in memory. Alternatively, the RV-LV time delay value may be initially specified by, for example, a physician or other medical professional, then programmed into the satellite pacer using an external programming device.

Depending upon the implementation, the interventricular delay may vary according to the ventricular rate and so the synchronization controller may need to automatically adjust the RV-LV rate based on the RV rate. In any case, at step 824, the synchronization controller then applies the current value of the interventricular time delay to the expected timing of the next RV pulse to derive the timing for the next LV pulse. Hence, if the RV-LV delay is positive, the synchronization controller adds the interventricular delay to the time value of the next expected to RV pulse so that the next LV pulse will be delivered after that RV pulse, but subject to the interventricular delay. If the RV-LV delay is negative, the synchronization controller subtracts and the delay amount from the time value of the next expected RV pulse so that the next LV pulse will be delivered prior to that RV pulse, but again subject to the specified interventricular delay. Finally, if an interventricular delay of zero specified, then the satellite pacer merely uses the same timing of the next expected RV pulse for delivering the next LV pulse. Once the timing for one or more upcoming LV pulses has been determined, processing returns to FIG. 12.

Figure 14:
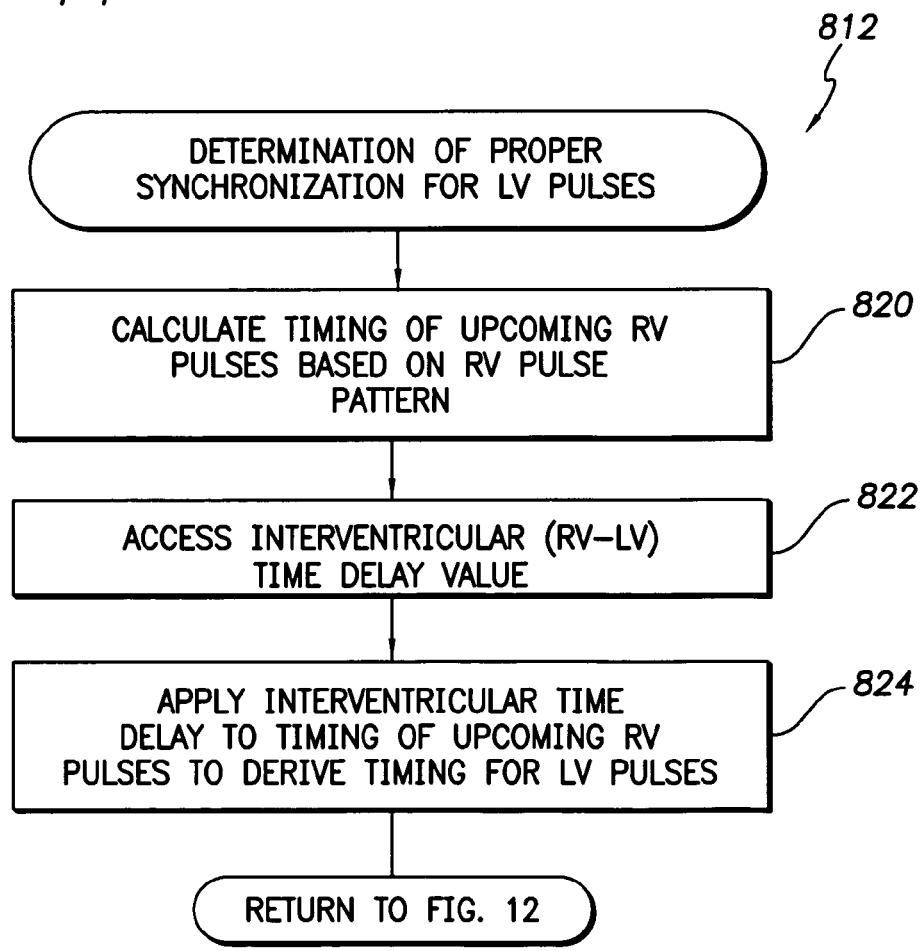
FIG. 14 is a flow diagram providing an exemplary technique for synchronizing supplemental pacing pulses to primary pulses for use with the technique of FIG. 12.

Thus, FIGS. 12-14 illustrate exemplary CRT techniques wherein the timing pattern of RV pulses delivered by a primary pacing device is communicated to the satellite pacer via encoded RV pulses. Principles may be applied to pacing pulses delivered by a primary pacing device to other chambers of the heart as well, not just RV pulses. In many implementations, simple encoding/synchronization techniques may be sufficient. For example, for patients who are paced primarily at only a constant rate, such as at a base rate, it may be sufficient to provide a satellite device capable of just tracking a constant rate. As noted above, many patients are paced 99% of the time at base rate. Thus, although their primary pacer may be capable of more sophisticated pacing, it is rarely used. For such patients, it is typically sufficient to provide a primary pacer capable of communicating a fixed RV rate to the satellite pacer via encoded pulses. During the relatively brief periods of time when the primary pacer is not pacing at a constant rate, the primary device can control the satellite to suspend satellite pacing via an appropriate command encoded within an RV pulse. When the primary pacer resumes constant rate pacing, the new rate is communicated to the satellite pacer via an encoded pulse along with instructions to resume satellite pacing. More comprehensive pacing schemes have been described herein, in part, for the sake of completeness.

Figure 15:
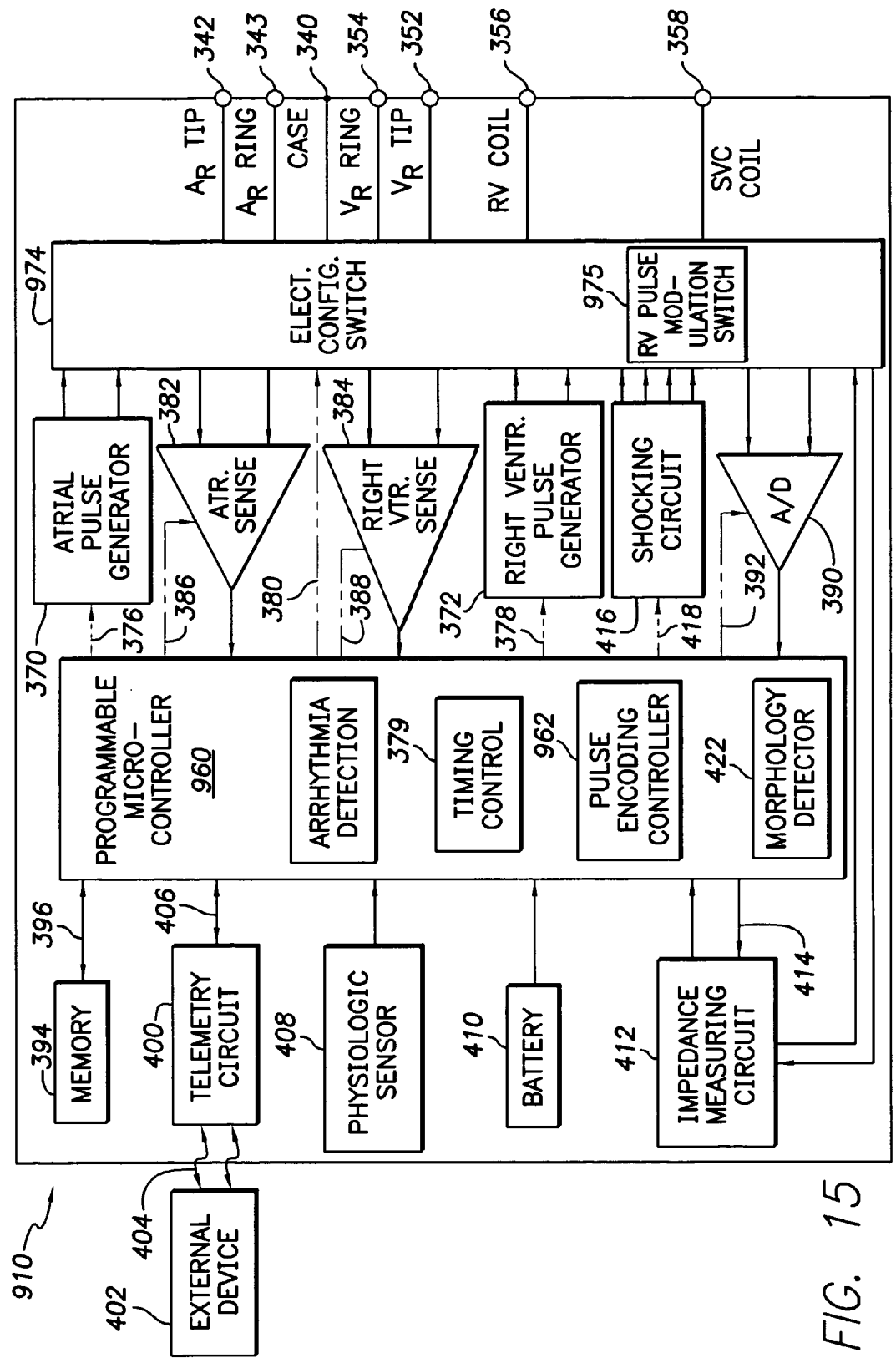
FIG. 15 is a functional block diagram of pertinent components of an alternative implementation of the primary pacing device of FIG. 7 that is equipped to encode information within modulated RV pulses in accordance with the techniques of FIGS. 10-14.
Figure 16:
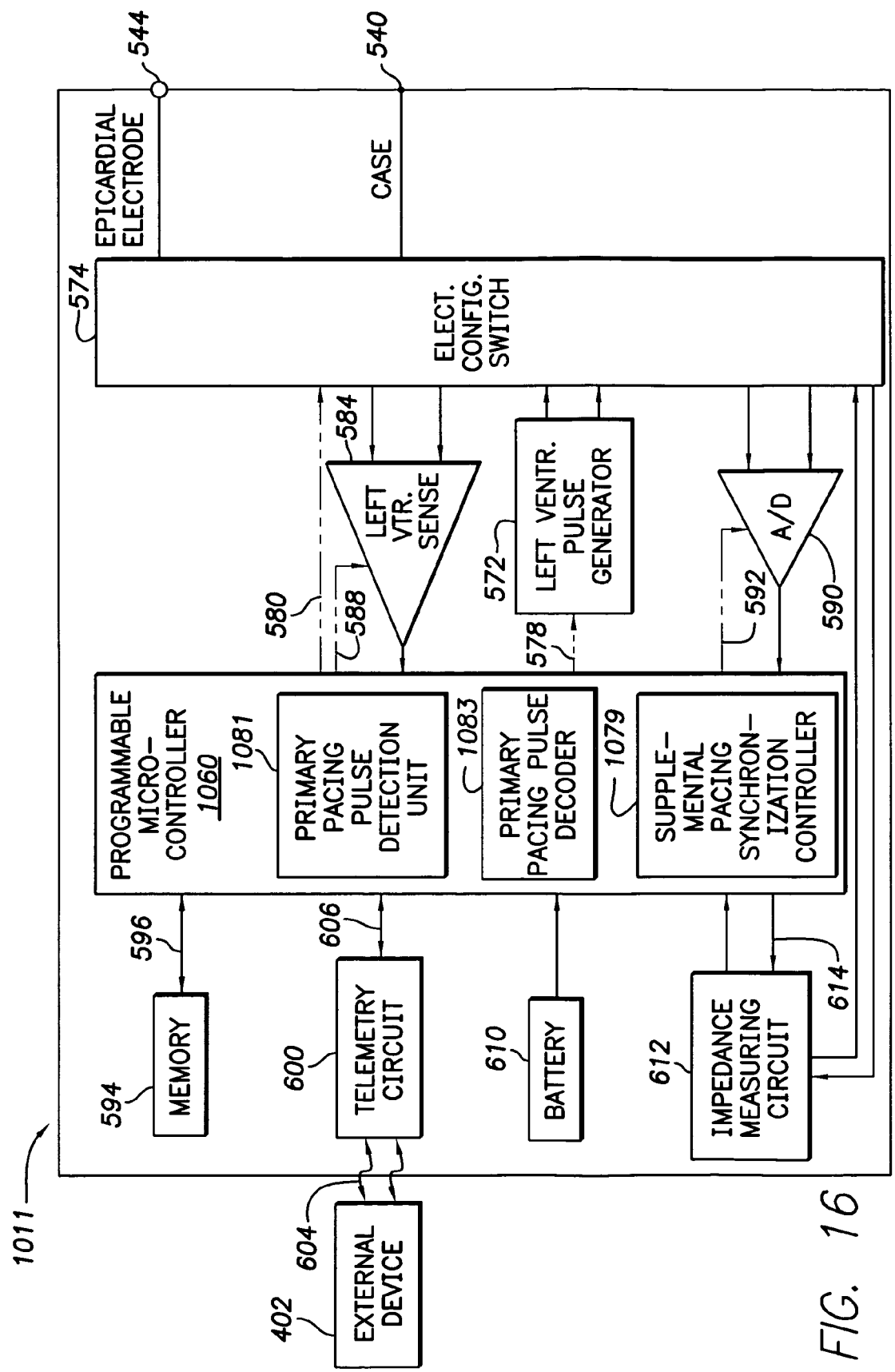
FIG. 16 is a functional block diagram of pertinent components of an alternative implementation of the satellite pacing device of FIG. 7 that is equipped to decode the modulated RV pulses in accordance with the techniques of FIGS. 10-14.

For the sake of completeness, a description of exemplary primary pacer/ICD and satellite pacing devices for use implementing the techniques of FIGS. 10-14 will now be provided with reference to FIGS. 15-16. The techniques of the invention, however, may be performed using any suitable implantable components. FIG. 15 illustrates a primary pacing device 910, which is similar to device 10 of FIG. 8, but additionally equipped to encode information for communication to a satellite pacer by modulating pacing pulses. Most of the components of device 910 may be the same as those of device 10, and so only pertinent differences will be addressed. Within device 910, a modified microcontroller 960 is provided which, in addition to components already described with reference to FIG. 8, includes a pulse encoding controller 962. A modified switch 974 is provided which, in addition to components already described with reference to FIG. 8, includes an RV pulse modulation switch 975. Pulse encoding controller 962 operates to encode information within pacing pulses delivered to the RV via the RV electrodes using the encoding techniques described with reference to FIGS. 10-14. More specifically, the controller determines the pattern of pulse portions/intervals to be employed, then controls modulation switch 975 to modulate the shape of the pulse so as to encode the information.

Collectively, RV pulse generator 372, modulation switch 975 and encoding controller 962 comprise an encodable pulse generator operative to generate and encode a therapeutic electrical stimulation pulse for delivery to patient tissues, with the pulse encoded with information to be communicated to a separate implantable device. Selected electrode terminals of device 910 and selected leads attached thereto comprise a pulse delivery system operative to deliver the encoded pulse to patient tissues. The RV pulse generator 372, modulation switch 975 and encoding controller 962 may also be regarded as providing means for generating an encoded therapeutic electrical stimulation pulse for delivery to patient tissues, wherein the pulse is encoded with information to be communicated to a second device. Although not shown, if the satellite device is also equipped to communicate information via encoded pulses, the primary device of FIG. 15 may additionally includes components for detecting, decoding and responding to the satellite pacing pulses. If so, the primary device may be equipped with components similar to those described below with reference to FIG. 16 for use in detecting and decoding LV pulses to extract encoded information. In particular, the satellite device may include components analogous to primary pacing pulse detection unit 1081 and primary pacing pulse decoder 1083 of FIG. 16 but adapted for use to decode LV pulses.

FIG. 16 is a simplified block diagram of satellite pacing device 1011, which is similar to device 11 of FIG. 9 but is equipped to detect and decode information encoded with primary pacing pulses. That is, satellite pacing device 1011 is capable, at least, of detecting and decoding primary (i.e. RV) pacing pulses in the heart and selectively providing supplemental (i.e. LV) pacing pulses to the left ventricles synchronized with the primary pulses. As most of the components of device 1011 may be the same as those of device 910, only pertinent differences will be addressed.

The microcontroller 1060 includes a primary pacing pulse detection unit 1081, which processes signals received via sense amplifier 584 to identify primary pacing pulses therein. A primary pacing pulse decoder 1083 analyzes the shape of each primary pulse to determine whether information is encoded therein and, if so, to decode the information using the techniques discussed above. Information extracted from the primary pacing pulses is forwarded to a pacing synchronization controller 1079 so that the synchronization controller can determine the timing pattern of upcoming primary pulses based on the encoded information and further specify the timing pattern for delivering supplemental pacing pulses in synchronization with upcoming primary pacing pulses. Microcontroller 1060 may also be configured to respond to any other information encoded within the primary pulses, such as command or control information. In one specific example, the microcontroller activates or deactivates delivery of supplemental pacing pulses based on commands received from the primary pacer via encoded pulses.

Collectively, the primary pacing pulse detection unit 1081 and the primary pacing pulse decoder 1083 comprise an encodable pulse detector operative to detect an encoded therapeutic stimulation pulse within patient tissues generated by a separate implantable device and to decode the pulse to extract encoded information. Remaining components of the microcontroller 1060, including pacing synchronization controller 1079, provide a control system that is operative to control delivery of therapy in response to the encoded information. The primary pacing pulse detection unit 1081 and the primary pacing pulse decoder 1083 may also be regarded as a means for detecting an encoded therapeutic stimulation pulse within patient tissues and for decoding the pulse to extract the encoded information. Although not shown, the satellite device may also be equipped to communicate information to the primary device of FIG. 15 via encoded pulses. If so, the satellite device may be equipped with components similar to those described above with reference to FIG. 15 for controlling the encoding of information and for modulating LV pulses to represent the encoded information. In particular, the satellite device may include components analogous to pulse encoding controller 962 and RV pulse modulation switch 975 of FIG. 15 but adapted to encode LV pulses.

What have been described are various systems and methods for implementing an implantable primary/satellite pacing system. However, principles of the invention may be exploited using other implantable systems or in accordance with other techniques. Thus, while the invention has been described with reference to particular exemplary embodiments, modifications can be made thereto without departing from the scope of the invention.

What is claimed is:

1. A method for communicating information between first and second implantable medical devices implanted within a patient, the method comprising:
generating a therapeutic electrical stimulation pulse using the first device, the stimulation pulse encoded with information to be communicated to the second device;
delivering the encoded therapeutic stimulation pulse to patient tissue in a first heart chamber;
detecting a far-field version of the therapeutic stimulation pulse within tissues of a second chamber of the patient's heart using the second device; and
decoding the detected pulse using the second device to extract the encoded information.

2. The method of claim 1
wherein the first implantable device is a primary cardiac pacemaker; and
wherein the step of delivering the therapeutic stimulation pulse to patient tissue is performed to deliver an encoded cardiac pacing pulse to cardiac tissue with a pulse magnitude sufficient to depolarize a portion of cardiac tissue.

3. The method of claim 2
wherein the second implantable device is a secondary cardiac pacemaker.

4. The method of claim 3
wherein the primary cardiac pacemaker is equipped to generate pacing pulses for delivery to the right ventricle (RV); and
wherein the step of delivering the encoded cardiac pacing pulse is performed to deliver the encoded pulse endocardially to the RV.

5. The method of claim 4
wherein the secondary cardiac pacemaker is an epicardial left ventricle (LV) satellite pacer equipped to sense electrical signals at the LV; and
wherein the step of detecting the therapeutic stimulation pulse using the second device is performed to detect a far-field version in the LV of the encoded pacing pulse delivered to the RV.

6. The method of claim 5 further including the step, performed by the LV epicardial satellite pacer, of generating LV pacing pulses for delivery to the LV based on the encoded information.

7. The method of claim 6 wherein the stimulation pulse is encoded with information indicating whether LV pulses are to be delivered by the epicardial satellite pacer.

8. The method of claim 6 wherein the stimulation pulse is encoded with information representative of a timing pattern of upcoming RV pulses.

9. The method of claim 8 wherein the second device determines a timing pattern for upcoming LV pulses based on the timing pattern of the upcoming RV pulses so as to synchronize the LV pulses with the RV pulses in accordance with cardiac resynchronization therapy techniques.

10. The method of claim 1 wherein the stimulation pulse is encoded by the first device by modulating the shape of the stimulation pulse.

11. The method of claim 10 wherein the stimulation pulse is modulated to include a sequence of individual pulse portions collectively configured to encode the information.

12. The method of claim 11 wherein the individual pulse portions are collectively configured to encode the information digitally.

13. The method of claim 12 wherein relative spacing between the individual pulse portions of the stimulation pulse is modulated to digitally encode the information.

14. The method of claim 12 wherein relative width of the individual pulse portions of the stimulation pulse is modulated to digitally encode the information.

15. The method of claim 11 wherein individual pulse portions have durations each in the range of 15-30 microseconds ($\mu$s) and wherein the total pulse has a duration in the range of 0.2-2.0 milliseconds (ms).

16. An implantable cardiac stimulation system for delivering cardiac stimulation therapy to the heart of a patient, the system having first and second separately implanted devices, comprising:

an encodable pulse generator provided within the first device and operative to generate an encoded therapeutic electrical stimulation pulse for delivery to patient tissues in a first heart chamber, the pulse encoded with information to be communicated to the second device; and an encodable pulse detector provided within the second device and operative to detect a far-field version of the encoded therapeutic stimulation pulse within patient tissues in a second chamber of the patient's heart and to decode the pulse to extract the encoded information.

17. The system of claim 16 wherein the first device is a primary cardiac pacemaker equipped with endocardial pacing leads and wherein the second device is a satellite cardiac pacemaker equipped with epicardial pacing leads.

18. An implantable cardiac stimulation system for delivering cardiac stimulation therapy to the heart of a patient, the system having first and second separately implanted devices, comprising:

means, provided within the first device, for generating an encoded therapeutic electrical stimulation pulse for delivery to patient tissues in a first chamber of the patient's heart, the pulse encoded with information to be communicated to the second device; and means, provided within the second device, for detecting a far field version of the encoded therapeutic stimulation pulse within patient tissues in a second chamber of the patient's heart and for decoding the pulse to extract the encoded information.

* * * * *

UNITED STATES PATENT AND TRADEMARK OFFICE
CERTIFICATE OF CORRECTION

PATENT NO.        : 7,630,767 B1                                                                Page 1 of 1
APPLICATION NO. : 11/440723
DATED             : December 8, 2009
INVENTOR(S)       : Poore et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 575 days.

Signed and Sealed this

Second Day of November, 2010

David J. Kappos
*Director of the United States Patent and Trademark Office*